US006898531B2

(12) United States Patent
Sheehan et al.

(10) Patent No.: US 6,898,531 B2
(45) Date of Patent: May 24, 2005

(54) ALGORITHMS FOR SELECTION OF PRIMER PAIRS

(75) Inventors: John B. Sheehan, Mountain View, CA (US); Daryl J. Thomas, Menlo Park, CA (US); Wade A. Barrett, Santa Clara, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 109 days.

(21) Appl. No.: 10/042,406

(22) Filed: Jan. 9, 2002

(65) Prior Publication Data

US 2003/0068625 A1 Apr. 10, 2003

Related U.S. Application Data

(60) Provisional application No. 60/317,311, filed on Sep. 5, 2001.

(51) Int. Cl.[7] .......................... G01N 33/48; G06F 19/00; C12Q 1/68
(52) U.S. Cl. ................ 702/19; 702/20; 435/6
(58) Field of Search ................ 702/19, 20; 435/6

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,800,159 A | 1/1989 | Mullis et al. | |
| 4,965,188 A | 10/1990 | Mullis et al. | |
| 5,512,462 A | 4/1996 | Cheng | |
| 6,007,231 A | 12/1999 | Vijg et al. | 364/497 |
| 6,150,094 A | 11/2000 | Maier et al. | |
| 6,214,557 B1 | 4/2001 | Barnes et al. | 435/6 |
| 6,231,812 B1 | 5/2001 | Rothberg et al. | 422/68.1 |
| 6,391,559 B1 | 5/2002 | Brown et al. | 435/6 |

FOREIGN PATENT DOCUMENTS

| DE | 10062566 A1 | 6/2002 |
|---|---|---|
| WO | 9911823 | 3/1999 |

OTHER PUBLICATIONS

Harris, N.L. Genotator: A Workbench for Sequence Annotation. Genome Research. 1997. vol. 7, pp. 754–762.*
Primer3, Release 0.6. Whitehead Institute for Biomedical Research. 1997. pp. 1–20.*
Harris, N.L. Genotator: A Workbench for Sequence Annotation. Genome Methods. 1997. vol. 7, pp. 754–762.*
Univ. of Washington Genome Center, 8 pp. printed Nov. 26, 2001 from www.genome.washington.edu.
*Repbase update*, Genetic Information Research Institute, 2001, 4 pp. printed Nov. 26, 2001 from www.girinst.org.
Virtual Genome Center info., *Info. about xprimer*, 4. pp. printed Nov. 26, 2001 from alces.med.umn.edu.
*Primer3*, 5 pp. printed Nov. 26, 2001 from www–genome.wi.mit.edu.
*Long PCR reagents & Guidelines*, 3 pp. printed Jun. 15, 2000 from twod.med.harvard.edu.
*Tools for data mining*, NCBI GenBank, 4 pp. printed Nov. 26, 2001 from www.ncbi.nlm.nih.gov.
*Electronic PCR*, NCBI GenBank, 2 pp. printed Nov. 26, 2001 from www.ncbi.nlm.nih.gov.
Boehringer Mannheim, PCR Applications Manual, Boehringer Mannheim GmbH, Biochemica, Germany, pp. 23, 27–53 and 109, 1995.
Newton, CR, PCR Essential Data, published by Wiley & Sons, Inc. New York, pp. 3, 24, 25, 53, 72–86, 1995.
Gorelenkov, A., et al., "Set of Novel Tools for PCR Primer Design", *BioTechniques* 31(6):1326–1330 (2001).
Proutski, V., et al., "Primer Master: a new program for the design and analysis of PCR primers", *Cabios* 12(3):253–255 (1996).
Doi, K., et al., "Greedy Algorithms for Finding a Small Set of Primers Satisfying Cover and Length Resolution Conditions in PCR Experiments", *Genome Informatics Series* 8:43–52 (1997).
Plasterer, T., "Primerselect: Primer and Probe design", *Methods in Molecular Biology* 70:291–302 (1997).
Podowski, R., et al., "MEDUSA: large scale automatic selection and visual assessment of PCR primer pairs", *Bioinformatics* 17(7): 656–657 (2001).
Kampke, T., et al., "Efficient primer design algorithms", *Bioinformatics* 17(3):214–225 (2001).
Pesole, G., et al., "GeneUp: A Program to Select Short PCR Primer Pairs that Occur in Multiple Members of Sequence Lists", *BioTechniques* 25:112–123 (1998).
Cormen, T.H. et al., *Contents—Introduction to Algorithms*, 1994, 10 pp., MIT.
Sanchez, G. et al., *Relative amplification efficiency of differently sized templates by long–distance PCR*, BioTechniques, Mar. 1998, pp. 400–402, vol. 24, No. 3.
Barnes, W.M., *PCR amplification of up to 35–kb DNA with high fidelity and high yield from λ bacteriophage*, Proc. Natl. Acad. Sci. USA, Mar. 1994, pp. 2216–2220, vol. 91, Genetics.
Cheng, S., et al., *Effective amplification of long targets from cloned inserts and human genomic DNA*, Proc. Natl. Acad. Sci. USA, Jun. 1994, pp. 5695–5699, vol. 91, Genetics.
Cohen, Jon. *'Long PCR' leaps into larger DNA sequences*, SCIENCE, Mar. 18, 1994, pp. 1564–1565, vol. 263.
Cheng, S., et al., *Long PCR*, NATURE, Jun. 23, 1994, pp. 684–685, vol. 369.

(Continued)

*Primary Examiner*—Marianne P. Allen
*Assistant Examiner*—Channing S. Mahatan
(74) *Attorney, Agent, or Firm*—Gulshan H. Shaver; Deana A. Arnold

(57) ABSTRACT

The presently claimed invention provides methods for amplifying a DNA target sequence. One embodiment of the present invention provides robust methods for amplification of target sequences. In a first aspect of the invention, a method for designing primer pairs for the amplification reaction is provided. In a further aspect of the invention, reagents and cycling parameters for the amplification reaction are provided.

25 Claims, 8 Drawing Sheets

OTHER PUBLICATIONS

Zhang, L–H, et al., *Long–distance PCR–based strategy for preparing knock–in vectors directly from ES cell genomic DNA*, BioTechniques, Nov. 1998, pp. 784–788, vol. 25.

Loukianov, E.V., et al., *Identification of targeted embryonic stem cells using long–distance PCR*, BioTechniques, Sep. 1997, pp. 376–380, vol. 23.

Taylor, G.R., et al., *The polymerase chain reaction: from functional genomics to high–school practical classes*, Current Opinion in Biotechnology, 1998, pp. 35–42, vol. 9, Current Biology Ltd.

Min, G–S, et al., *Long–distance genome walking using the long and accurate polymerase chain reaction*, BioTechniques, 1998, pp. 398–399, vol. 24, No. 3.

Sorokin, A., et al., *A new approach using multiplex long accurate PCR & yeast artificial chromosomes for bacterial chromosome mapping & sequencing*, Genome Research, 1996, pp. 448–453, vol. 6, Cold Spring Harbor Lab. Press.

Ohya, Y., *LA–PCR–based quick method for identification of genes responsible for complementation of saccharomyces cerevisiae mutations*, BioTechniques, May 1996, pp. 772–778, vol. 20, No. 5.

Cheng, S., et al., *XL PCR amplification of long targets from genomic DNA*, Methods in Molecular Biology, pp. 17–29, vol. 67: PCR Cloning Protocols: From Molecular Cloning to Genetic Engineering, Humana Press Inc.

Foord, O.S., et al., *Long distance PCR*, PCR Methods & Applications, 1994, pp. S149–S161, vol. 3, Cold Spring Harbor Lab.

Ohler, L.D., et al., *Optimization of long–distance PCR using a transposon–based model system*, PCR Method & Applications, 1992, pp. 51–59, vol. 2, Cold Spring Harbor Lab. Press.

Ponce, M.R., et al., *PCR amplification of long DNA fragments*, Nucleic Acid Research, 1992, pp. 623, vol. 20, No. 3, Oxford Univ. Press.

Lindberg, A.M., et al., *Amplification & closing of complete enterovirus genomes by long distance PCR*, Journal of Virological Methods, 1997, pp. 191–199, vol. 65, Elsevier Science BV.

Akasaka, T., et al., *Long distance polymerase chain reaction for detection of chromosome translocations in B–cell lymphoma/leukemia*, LEUKEMIA, Apr. 1997, cover page & pp. 316–317, vol. 11, supp. 3.

Takita, Y., et al., *Applications of long & accurate polymerase chain reaction method in yeast molecular biology: direct sequencing of amplified DNA and its introduction into yeast*, YEAST, 1997, pp. 763–768, vol. 13, John Wiley & Sons. Ltd.

Hengen, P.H., *Optimizing multiplex & LA–PCR with betaine*, TiBS, 1997, cover & pp. 225–226, 1997, vol. 22, Int'l. Union of Biochemistry & Elsevier Trends Journal.

*Long–range PCR: synthesis of products independent of size*, TIG, Nov. 1996, cover & p. 458, vol. 12, No. 11.

Maga, E.A., et al., *Amplification of a 9.0–kb fragment using PCR*, BioTechniques, Jul. 1991, index & pp. 185–186, vol. 11, No. 1, Eaton Publishing Co.

Lay, J.M., et al., *Rapid conformation of gene targeting in embryonic stem cells using two long–range PCR techniques*, Transgenic Research, 1998, pp. 135–140, vol. 7, Chapman & Hall.

Luthra, R., et al., *Mapping of genomic t(2;5)(p23;q35) break points . . .* , Hematopathology & Molecular Hematology, 1998, pp. 173–183, vol. 11 (3&4), Marcel Dekker, Inc.

Akasaka, T., et al., *Polymerase chain reaction amplification of long DNA targets . . .* , Int'l Journal of Oncology, 1998, pp. 113–121, vol. 12.

Hengen, P.N., *Long and accurate PCR*, TiBS, 1994, cover & pp. 341–342, vol. 19, Int'l Union of Biochemistry & Elsevier Trends Journal.

*Expand long template PCR system*, Specification, ROCHE, Jun. 1999, 4 pp., vers. 3.

*Expand long template PCR system*, Specification, ROCHE, Sep. 1999, 5 pp., vers. 4.

*Long–range PCR using the expand long template PCR kit*, Boehringer Mannheim, 2 pp.

* cited by examiner

CAACTAAAAGTCACAAAAGCCATGGAAAATAGTCTCAGGGATACACATCTGCTC
TTCAGATTCTGAATTCTGGTCTTGCATGATTTCTTTCACCAGGAGCCAGCAGAG
CTGTGCTTCCTCGGACTAACAACTTGCCCCTCACTCCCTACCCTCCGGGCACCG
TCTCCTCTATAAAGTCACCCTCTCAGCTTTTCTTTATCCCCAGAGATGACACAA
ATACAGAGAACTGTGGCATTTTTATAGCATTTAGGTGAAAGATGTTATAAATTA
TACAGTTCACCTGAGAGAAAAAATACATGCTAAACCAGCAGTGCCTCACACCT
GTAATCCCAGCATTTGGGGAGGCCAAAGCGGGAGGATTGCTTCAGCCCAGAGTT
CAAGATCAGACTGGGCAACACAGTGAGACCTCTTCTCTACAAAAAAAAAAAAAA
TCAAAAAATGAAGGAGGATCACTTGAGCTCTGGAGGTTGAGGCTGCAATGAGCC
ATGATTGCACCATTGCACTCTTGCCTGGGTGACAGAGTGAGACCCTGCCTCAAA
AAAAAAATAAATAAATAAATAGAAAGAAAGAAAGAAAATGAAAGAAGAAAATCC
ATGTGAATAATCTTATTCTAGCAAATAAGGATGTTAGAATGCAGCATATTAAAA
TATTACAAAAGTACAATACTATGAAAAAATATGGCACTCAACACAGAGCAGAAT
GGAAACTAGAATTGAACAGAGGAAAGTATTTTGAACTCCTGAGTGCAGGATAGG
TTTTTTTCAATAGATGGTATTGGGACAACTATTTGAAACAAAAAGAAATGTAG
ATCCACTAAATGAATTGTTCCTGGAATACAGACTTAAATAGATAA

CAACTAAAAGTCACAAAAGCCATGGAAAATAGTCTCAGGGATACACATCTGCTC
TTCAGATTCTGAATTCTGGTCTTGCATGATTTCTTTCACCAGGAGCCAGCAGAG
CTGTGCTTCCTCGGACTAACAACTTGCCCCTCACTCCCTACCCTCCGGGCACCG
TCTCCTCTATAAAGTCACCCTCTCAGCTTTTCTTTATCCCCAGAGATGACACAA
ATACAGAGAACTGTGGCATTTTTATAGCATTTAGGTGAAAGATGTTATAAATTA
TACAGTTCACCTGAGAGAAAAAATACATGCTAAACCAGNNNNNNNNNNNNNNNN
NNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNN
NCAAAAAATGANNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNN
NNNNNNNNNNNNNNTATTCTAGCAAATAAGGATGTTAGAATGCAGCATATTAAAA
TATTACAAAAGTACAATACTATGAAAAAATATGGCACTCAACACAGAGCAGAAT
GGAAACTAGAATTGAACAGAGGAAAGTATTTTGAACTCCTGAGTGCAGGATAGG
TTTTTTTCAATAGATGGTATTGGGACAACTATTTGAAACAAAAAGAAATGTAG
ATCCACTAAATGAATTGTTCCTGGAATACAGACTTAAATAGATAA

ALGORITHMS FOR SELECTION OF PRIMER PAIRS

CROSS REFERENCE TO RELATED APPLICATIONS

This application claims priority to provisional application U.S. Ser. No. 60/317,311 filed Sep. 5, 2001, entitled "Amplification of Nucleic Acids" which is incorporated by reference in its entirety for all purposes.

COPYRIGHT NOTICE

A portion of the disclosure of this patent document contains material which is subject to copyright protection. The copyright owner has no objection to the xerographic reproduction by anyone of the patent document or the patent disclosure exactly as it appears in the Patent and Trademark Office patent file or records, but otherwise reserves all copyrights whatsoever.

BACKGROUND OF THE INVENTION

The polymerase chain reaction (PCR) is a powerful method for amplifying nucleic acid sequences. Various disclosures involving this technique are found in U.S. Pat. Nos. 4,683,202; 4,683,195; 4,800,159; 4,965,188; and 5,512,462, each of which is incorporated herein by reference. In a simple form, PCR is an in vitro technique for the enzymatic synthesis of specific DNA sequences using two oligonucleotide primers that hybridize to complementary nucleic acid strands and flank a region that is to be amplified in a target DNA. A series of reaction steps of 1) template denaturation, 2) primer annealing, and 3) extension of annealed primers by DNA polymerase, results in the geometric accumulation of a specific fragment whose termini are defined by the 5' ends of the primers. As is well known, PCR is capable of selective enrichment of specific DNA sequences by a factor of $10^9$.

PCR has been applied widely in molecular biology for sequencing, genome mapping and forensics. However, despite such wide-spread use, amplifying long stretches of DNA, particularly genomic DNA, is difficult. Many protocols for long range PCR exist; however, reaction conditions are usually optimized for amplifying specific target regions of interest. Applying the same "optimized" reaction conditions to amplify a different target region may not result in a detectable amplification product.

In light of the above limitations, there is a need in the art for methods capable of amplifying nucleic acid sequences. The resulting methods may be used in some embodiments to amplify mammalian target sequences across the genome to facilitate genotyping studies, and for other applications in the art of molecular biology.

SUMMARY OF THE INVENTION

The presently claimed invention provides methods for amplifying a DNA target sequence. One embodiment of the present invention provides robust methods for amplification of target sequences. In a first aspect of the invention, a method for designing primer pairs for the amplification reaction is provided. In a further aspect of the invention, reagents and cycling parameters for the amplification reaction are provided.

Thus, the present invention provides a method for designing primer pairs for amplifying a target sequence, comprising the steps of: choosing a reference sequence; removing at least selected repeat regions in the reference sequence to yield removed and unremoved reference sequence; selecting primer sequences from the unremoved reference sequence according to two or more parameters including primer length and primer melting temperature to yield a set of primers; evaluating the set of primers for extent of coverage and overlap of the reference sequence; and selecting a subset of primer pairs having reduced overlap from the set of primers.

In addition, the present invention provides a method for amplifying a target sequence, comprising the steps of: mixing a reaction cocktail comprising deoxynucleotide triphosphates, target DNA, a divalent cation, DNA polymerase enzyme, a broad spectrum solvent, a zwitterionic buffer and at least one primer pair designed by the method above; heating the reaction cocktail at a denaturing temperature of about 90.0° C. to about 96.0° C. for about 1.0 second to about 30.0 seconds; cooling the reaction cocktail at an annealing/extension temperature of about 50.0° C. to about 68.0° C. for about 1.0 minute to about 28.0 minutes; repeating the heating and cooling steps at least 10 times; and cooling the reaction cocktail to 4.0° C. in a final cooling step.

Other and further objects, features and advantages would be apparent and eventually more readily understood by reading the following specification and by reference to the accompanying drawings forming a part thereof, or any examples of the presently preferred embodiments of the invention given for the purpose of the disclosure.

DETAILED DESCRIPTION OF THE FIGURES

FIG. 8 shows an exemplary sequence before (SEQ ID NO:1) and after (SEQ ID NO:2) removal of repeat sequences (underlined).

DETAILED DESCRIPTION OF EMBODIMENTS OF THE INVENTION

Reference now will be made in detail to various embodiments and particular applications of the invention. While the invention will be described in conjunction with the various embodiments and applications, it will be understood that such embodiments and applications are not intended to limit the invention. On the contrary, the invention is intended to cover alternatives, modifications and equivalents that may be included within the spirit and scope of the invention. In addition, throughout this disclosure various patents, patent applications, websites and publications are referenced. Unless otherwise indicated, each is incorporated by reference in its entirety for all purposes.

The term "a" or "an" as used herein in the specification may mean one or more. As used herein in the claim(s), when used in conjunction with the word "comprising", the words "a" or "an" may mean one or more than one. As used herein "another" may mean at least a second or more.

Robust methods for designing primers and amplifying target sequences are described herein. In one specific embodiment of the present invention, amplification of between about 3 kilobases and about 15 kilobases or more in length has been achieved. The methods result in excellent fidelity of amplification and product yield for target sequences in general. In some applications of the present invention, the methods result in a greater than 95% success rate for amplification of mammalian genomic sequences genome-wide when a reference sequence and a target sequence are from the same species. However, in addition, the methods of the present invention can be used to amplify long target sequences genome-wide in species closely-related to the species from which a reference sequence was taken. For example, human sequence can be used to design primers that will produce long-range amplification products of non-human primates with a success rate of greater than 80%.

I. Primer Design

Figure 1:
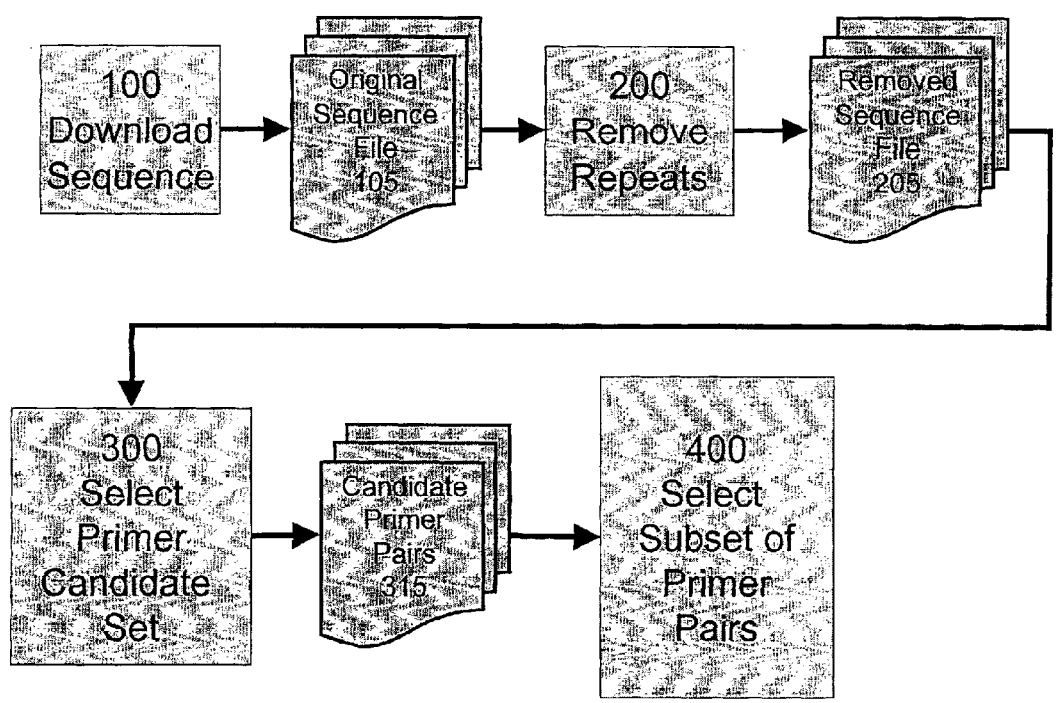
FIG. 1 is a flow chart showing the primer pair selection process.
Figure 7:
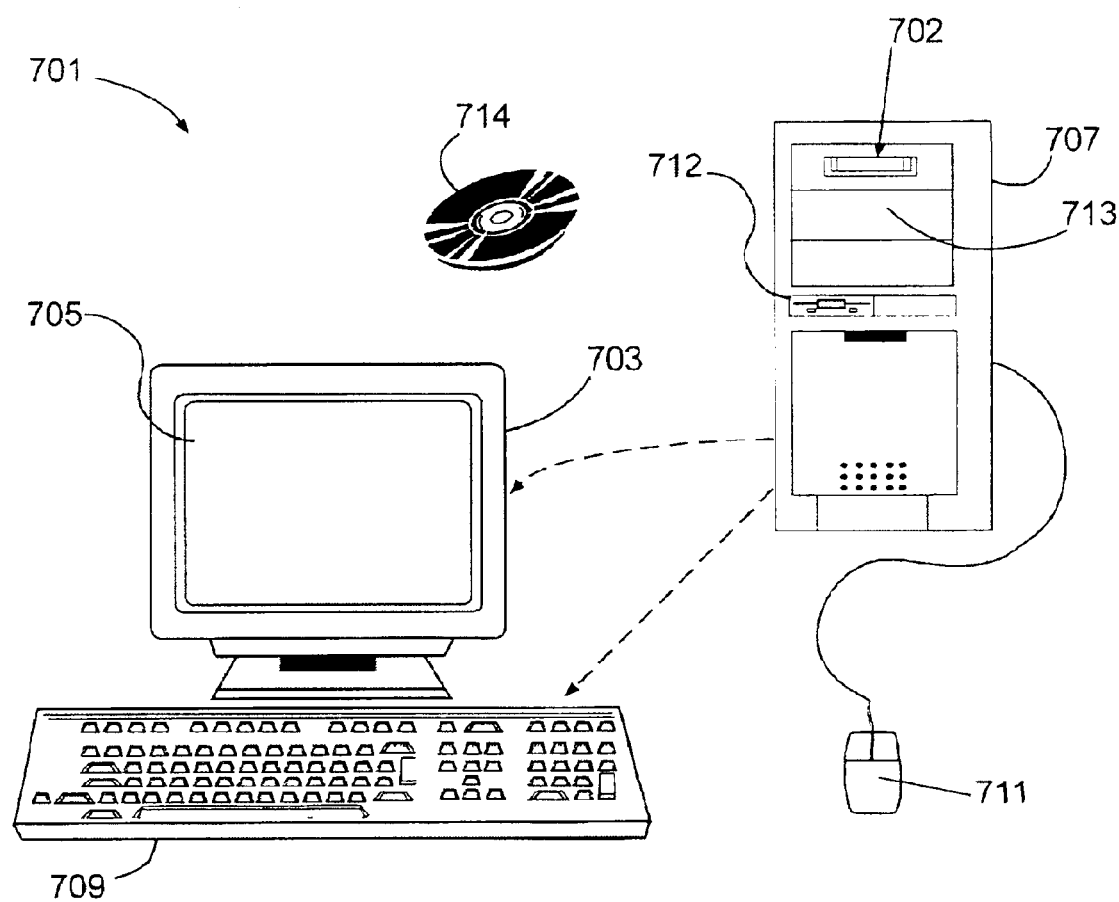
FIG. 7 shows a system that may be used for designing primer pairs.

One aspect of the invention is methods for primer design. FIG. 1 is a flow chart generally illustrating the primer selection process. In step 100 of primer design, a sequence of interest (target sequence or reference sequence) is selected for amplification and downloaded into a sequence file (original sequence file). The sequence file and the software for performing the analysis herein may be stored on a computer system such as shown in FIG. 7.

In step 200, repeat sequences, such as Alu and LINE sequences in the reference sequence, are "masked" or removed from the primer selection analysis. In step 300, the non-repetitive, un-removed sequences that remain are analyzed according to at least two selection parameters and a set of all primer candidates that fit within the chosen parameters is established. Such selection parameters include, for example, melting temperature, likelihood of primer-dimer formation between the primers, primer length, and the like. Any of the primers generated by the third step may be used in the amplification reactions of the present invention.

In step 400, the set of primers generated by the third step is evaluated for coverage and overlap of the target sequence and a subset of primers is chosen so as to reduce the number of primers needed to amplify the target sequence.

A. Generation of a Primer Set

In the first step 100, a sequence of interest (target sequence) may be obtained, for example, from public databases such as the Human Genome Project Working Draft team at the University of California at Santa Cruz, NCBI, The Sanger Center, Whitehead Institute for Biomedical Research Center for Genome Research, Washington University Genome Sequencing Center, US DOE Joint Genome Institute, or Riken Gene Bank. Sequence generated de novo also may be used.

The second step 200 may be performed by hand or by a computer software program such as, for example, the program available from the University of Washington called "RepeatMasker", a program that recognizes sequences that are repeated in the genome (A. F. A. Smit and P. Green, www.genome.washington.edu/uwgc/analysistools/repeatmask, incorporated herein by reference). Essentially, RepeatMasker screens genomic sequences for repeat regions in DNA, referencing a database of known repetitive elements called RepBase. RepBase Version 5 has been employed in the methods of the present invention, as have earlier versions of RepBase. The RepBase database can be licensed from the Genetic Information Research Institute (see www.girinst.org, incorporated herein by reference). Essentially, known repetitive sequences such as Single Interspersed Nuclear Elements (SINEs, such as alu and MIR sequences), Long Interspersed Nuclear Elements (LINEs such as LINE1 and LINE2 sequences), Long Terminal Repeats (LTRs such as MaLRs, Retrov and MER4 sequences), Transposons, MER1 and MER2 sequences are "masked" or removed by the RepeatMasker program by substituting each specific nucleotide of the repeated regions (A, T, G or C) with an "N" or "X". In addition, xprimer (alces.med.umn.edu, Virtual Genome Center, incorporated herein by reference), a primer selection tool described below, can be used to identify simple, complex and internal repeats from a small database of repeats. Also, NCBI offers an Electronic PCR feature through its website (ncbi.nlm.nih.gov, incorporated herein by reference). The Electronic PCR program removes repetitive sequences from a non-repetitive marker set.

FIG. 8 shows an exemplary sequence with repeat regions shown (underlined), then removed or "masked" by inserting "Ns". After the repeat regions are removed, primer pair candidates are selected from the unremoved sequence according to various parameters.

The third step 300 may be performed by hand or by a computer software program. For example, commercially available software such as Primer 3 (www-genome.wi.mit.edu/cgi-bin/primer/primer3, incorporated herein by reference), xprimer (alces.med.umn.edu, Virtual Genome Center, incorporated herein by reference), Oligo (Molecular Biology Insights, Inc., Cascade, Colo., incorporated herein by reference) or PrimerSelect (DNAStar, Inc., Madison, Wis., incorporated herein by reference) may be employed. Those with skill in the art may be familiar with other programs that are available for primer selection or can develop such a program. In one embodiment, a software program is used that allows one to dictate various primer parameters such as primer melting temperature, primer length, stringency of hybridization, existence of duplexes, specificity of hybridization, existence of a GC clamp, existence of hairpins, existence of sequence repeats, the dissociation minimum for a 3' dimer, the dissociation minimum for the 3' terminal stability range, the dissociation minimum for a minimum acceptable loop, percent maximum homology, percent consensus homology, the maximum number of acceptable sequence repeats, frequency threshold, or the maximum length of acceptable dimers and the like. Also, in choosing primers for the third step, the length of a first primer of a primer pair may be fixed at a specific length, and the length of a second primer of the primer pair may be adjusted so that the melting temperature of the second primer pair is substantially the same as the melting temperature of the first primer.

Primer3 is a computer program that suggests PCR primers for a variety of applications, for example, to create STSs (sequence tagged sites) for radiation hybrid mapping, or to amplify sequences for SNP discovery. Primer3 also can select single primers for sequencing reactions and can design oligonucleotide hybridization probes. In selecting oligos for primers or hybridization probes, Primer3 can consider many factors, including oligo melting temperature, length, GC content, 3' stability, estimated secondary structure, the likelihood of annealing to or amplifying undesirable sequences (for example interspersed repeats), the likelihood of primer-dimer formation between two copies of the same primer, and the accuracy of the source sequence. In the design of primer pairs, Primer3 can consider product size and melting temperature, the likelihood of primer-dimer formation between the two primers in the pair, the difference between primer melting temperatures, and primer location relative to particular regions of interest or regions to be avoided.

xprimer is another tool for selection of PCR primers. It is designed for selection of sets of primers along very large queries, where the primers must all fall within a relatively narrow melting temperature range. It is also useful in more traditional PCR applications. In xprimer, the actual primer sequences are printed to standard output with some statistical information. At the bottom of the display, a trace shows the log probability of the 3' end of the sequence occurring in genomic DNA as determined using a preformed database.

PrimerSelect is a suite of tools for the design and analysis of oligonucleotides, including primers for PCR, sequencing, probe hybridization and transcription. Using DNA, RNA or back-translated proteins as templates, PrimerSelect details thermodynamic properties for annealing reactions. The software lists all possible primers, ranked in order of suitability. PrimerSelect includes a virtual lab where one can predict the effects the selected primers on reading frames, restriction sites and other features. Additionally, PrimerSelect allows for loading sequences directly from NCBI's databases, so that primers may be designed for published sequence.

Oligo is a multi-functional program that searches for and selects oligonucleotides from a sequence file for PCR sequencing, site-directed mutagenesis, and various hybridization applications. Oligo calculates hybridization temperature and secondary structure of oligonucleotides based on the nearest neighbor change in free energy values.

B. Selection of a Subset of Primer Pairs

The fourth step of primer design involves evaluating the set of primer pairs generated in steps one through three for coverage and overlap of the target sequence, and selecting a subset of primer pairs from the set of primer pairs. This fourth step may be performed by hand or by a computer software program. Typically the goal of the fourth step is to choose the primer pairs that allow one to amplify all or substantially all of the entire target sequence with reduced sequence amplification overlap and/or a minimal or substantially minimal number of primer pairs.

In preferred embodiments, the algorithm is used to select primers that will amplify more than 90% of the unremoved target sequence, preferably more than 95% percent of the unremoved target sequence, and preferably more than 99% percent. Preferably the amplified portions of the unremoved target sequence overlap by less than 5%, preferably less than 2% and preferably less than 1%. Preferably a minimum or near minimum number of probe pairs is used.

Algorithms known in the art may be applied for this purpose. For example, shortest path algorithms may be used (see, generally, *Introduction to Algorithms*, Cormen, Leiserson, and Rivest, MIT Press, 1994, pp. 514–578, incorporated herein by reference). In a shortest-paths problem, a weighted, directed graph G=(V,E), with weight function w:E→R mapping edges to real-valued weights is given. The weight of path $p=(v_0, v_1, \ldots v_k)$ is the sum of the weights of its constituent edges:

$$w(p) = \sum_{i=1}^{k} w(v_{i-1}, v_i).$$

The shortest-path weight from u to v is defined by δ(u,v) being equal to min w(p):u←v if there is a path from u to v, otherwise, δ(u,v) is equal to infinity. A shortest path from vertex u to vertex v is then defined as any path p with weight w(p)=δ(u,v). Edge weights can be interpreted as various metrics; for example, distance, time, cost, penalties, loss, or any other quantity that accumulates linearly along a path that one wishes to minimize. In the embodiment of the shortest path algorithm used in applications of this invention, each primer pair was considered a "vertex". Bach primer pair vertex has a relationship to each other primer pair vertex. This relationship is an "edge" defined for each pair of vertices, with a "cost" for each edge. Cost is determined by parameters of choice, such as the extent of overlap of the vertices, the extent of gap between the vertices and a cost of adding another set of vertices to the final solution.

Single-source shortest-paths problems focus on a given graph G=(V,E), where a shortest path from a given source vertex s∈V to every vertex v∈V is determined. Additionally, variants of the single source algorithm may be applied. For example, one may apply a single-destination shortest-paths solution where a shortest path to a given destination vertex t from every vertex v is found. Reversing the direction of each edge in the graph reduces this problem to a single-source problem. Alternatively, one may apply a single-pair shortest-path problem where the shortest path from u to v for given vertices u and v is found. If the single-source problem with source vertex u is solved, the single-source shortest path problem is solved as well. Also, the all-pairs shortest-paths approach may be employed. In this case, a shortest path from u to v for every pair of vertices u and v is found—essentially, a single-source algorithm is run from each vertex.

One single-source shortest-path algorithm that may be employed in the methods of the present invention is Dijkstra's algorithm. Dijkstra's algorithm solves the single-source shortest-paths problem on a weighted, directed graph G=(V,E) for the case in which all edge weights are nonnegative. Dijkstra's algorithm maintains a set of vertices, S, whose final shortest-path weights from a source s have already been determined. That is, for all vertices v being elements of S, d[v]=δ(s,v). The algorithm repeatedly selects the vertex U as an element of V-S with the minimum shortest-path estimate, inserts u into S, and relaxes all edges radiating from u. In one implementation, a priority queue Q that contains all the vertices in V-S, keyed by their d values, is maintained. This implementation assumes that graph G is represented by adjacency lists.

Dijkstra (G, w, s)
1 INITIALIZE-SINGLE SOURCE (G,s)
2 S←∅
3 Q←V[G]
4 while Q≠∅
5 do u←EXTRACT-MIN (Q)
6 S←S∪{u}
7 for each vertex v∈Adj[u]
8 do RELAX (u,v,w)

Thus, G in this case is the graph of linear coverage of the target sequence, Q is the queue of all vertices to be evaluated and S is the set of vertices selected. Once one set of vertices (pair of primer pairs) is selected that covers a particular area of the target sequence, the other vertices that include these pairs can be discarded.

Other algorithms that may be used for selecting the subset of primers include a greedy algorithm (again, sec, *Introduction to Algorithms*, Cormen, Leiserson, and Rivest, MIT Press, 1994, pp. 329–355). A greedy algorithm obtains an optimal solution to a problem by making a sequence of choices. For each decision point in the algorithm, the choice that seems best at the moment is chosen. This heuristic strategy does not always produce an optimal solution. Greedy algorithms differ from dynamic programming in that in dynamic programming, a choice is made at each step, but the choice may depend on the soluations to subproblems. In a greedy algorithm, whatever choice seems best at the moment is chosen and then subproblems arising after the choice is made are solved. Thus, the choice made by a greedy algorithm may depend on the choices made thus far, but cannot depend on any future choices or on the solutions to subproblems. In this case, the algorithm is "greedy: in selecting the "best" primer pair at a moment in time according to selected criteria, without regard to how this selection will affect what primer pairs are available for future selection.

One variation of greedy algorithms is Huffman codes. A Huffman greedy algorithm constructs an optimal prefix code and the algorithm builds a tree T corresponding to the optimal code in a bottom-up manner. It begins with a set of |C| leaves and performs a sequence of |C|−1 "merging" operations to create the final tree. For example, assuming C is a set of n characters and that each character c∈C is an object with a defined frequency f[c], a priority queue Q, keyed on f, is used to identify the two least-frequent objects to merge together. The result of the merger of two objects is a new object whose frequency is the sum of the frequencies of the two objects that were merged. For example:

1 n←|C|
2 Q←C
3 for i←1 to n−1
4 do z←ALLOCATE-NODE( )
5 x←left[z]←EXTRACT-MIN(Q)
6 y←right[z]←EXTRACT-MIN(Q)
7 f[z]←f[x]+f[y]
8 INSERT (Q,z)
9 return EXTRACT-MIN(Q)

Line 2 initializes the priority queue Q with the characters in C. The for loop in lines 3–8 repeatedly extracts the two nodes x and y of lowest frequency from the queue, and replaces them in the queue with a new node z representing their merger. The frequency of z is computed as the sum of the frequencies of x and y in line 7. The node z has x as its left child and y as its right child. After n−1 mergers, the one node left in the queue—the root of the code tree—is returned in line 9.

Thus, one aspect of the present invention provides a method for designing primer pairs for amplifying a target sequence, comprising the steps of choosing a reference sequence; removing selected repeat regions in the reference sequence to yield removed and unremoved reference sequences; selecting primer sequences from the unremoved reference sequences according to one or more parameters to yield a set of primers; evaluating the set of primers for extent of overlap and coverage of the reference sequence; and selecting a subset of primer pairs having reduced overlap from the set of primers. In one embodiment of this aspect of the invention, the removing step is performed by a computer program that references a database of known repeat sequences. In a specific embodiment of this aspect of the invention, the database is RepBase. Also in a specific embodiment of the present invention, the computer program that performs the removing step is RepeatMasker. Another embodiment of this aspect of the present invention provides that one of the one or more parameters from the first selecting step be, for example, parameters available for selection in commercially-available primer selection programs such as Oligo, xprimer, PrimerSelect, Primer 3 and the like. Such parameters include primer melting temperature, primer length, stringency, existence of duplexes, specificity, GC clamp, existence of hairpins, existence of sequence repeats, dissociation minimum for 3' dimer, dissociation minimum 3' terminal stability range, dissociation minimum for minimum acceptable loop, percent maximum homology, percent consensus homology, maximum number of acceptable sequence repeats, frequency threshold, or maximum length of acceptable dimers.

Also, in an embodiment of the present invention, the second selecting step selects a subset of primer pairs where this subset has a reduced number of primer pairs required to amplify the target sequence. Preferably, the subset is a substantially minimal number of primer pairs required to amplify the target sequence. In one embodiment, the second selecting step selects the subset of primer pairs according to additional parameters such as length of the overlap of the target sequence amplified by the primer pairs, existence of gaps of target sequence between primer pairs, and the necessity of adding another primer pair to the subset. In an embodiment of this aspect of the invention, the second selecting step is performed by a computer program. Such a program may apply a shortest-paths algorithm or greedy algorithm, and in one embodiment of the present invention, the computer program applies Dijkstra's single-source shortest paths algorithm (see FIGS. 2 and 3).

Figure 2:
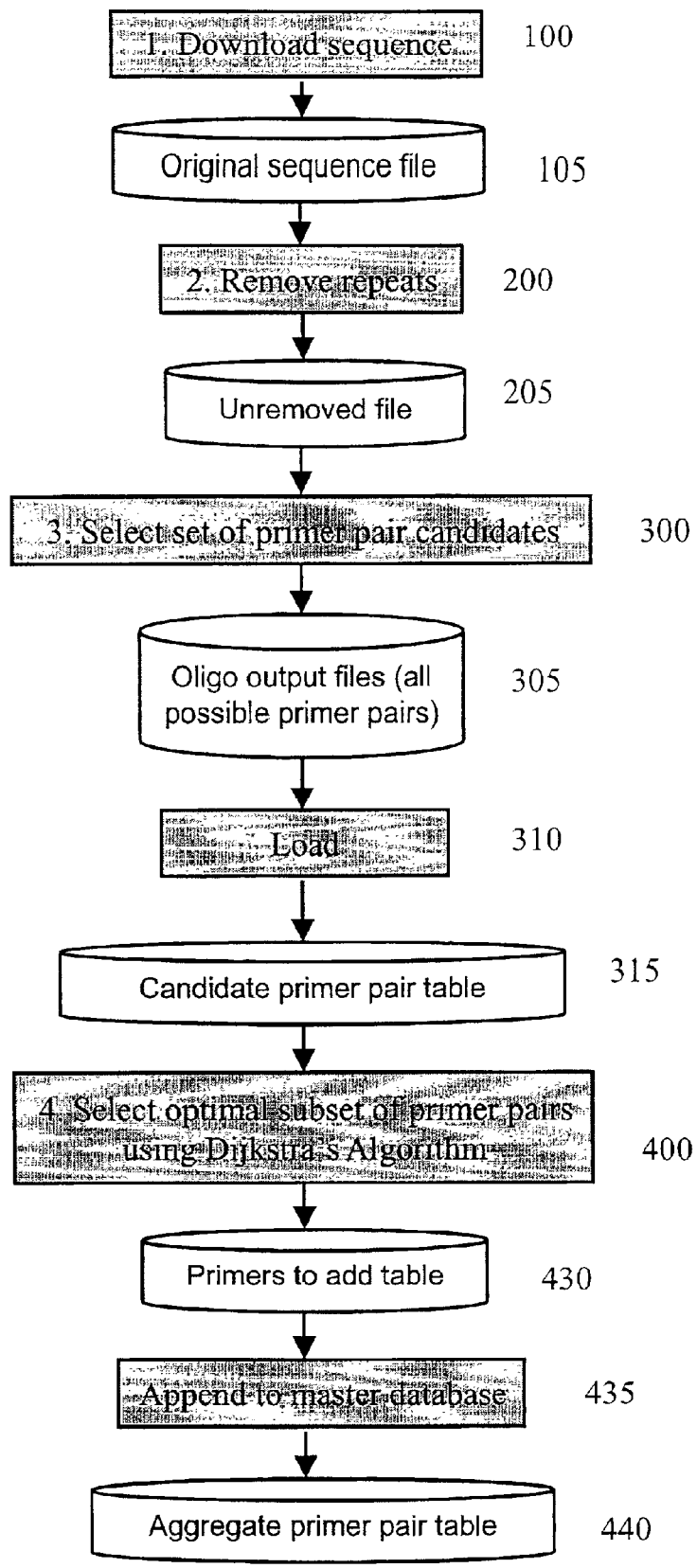
FIG. 2 is a flow chart showing a detailed primer pair selection process according to one embodiment of the present invention.

FIG. 2 shows one embodiment of the process in FIG. 1 in greater detail. At step 100, the target or reference sequence is downloaded from, for example, a public database, and stored in an original sequence file (105). At step 200, repeat sequences in the target sequence are removed from the primer selection process by, for example, a computer program such as RepeatMasker. A file of the unremoved sequence (205) is stored on a server or similar memory device. At step 300, primer pair candidates are selected in accordance with established, selected parameters, and these primer pair candidates are stored in a file (305) on a server or similar memory device. Preferably, all possible primer pairs that fall within the established parameters are stored in file 305. At step 310, the file of all possible primer pairs is parsed, loaded and a candidate primer pair table (315) is generated. At step 400, a subset of primer pairs is selected by applying, for example, a greedy algorithm. The subset of primer pairs is stored in file 430, a "primers to add" table, on a server or similar memory device. The primers to add table is then appended to a master database in step 435, adding this subset of primer pairs to an aggregate primer pair table 440.

Figure 3:
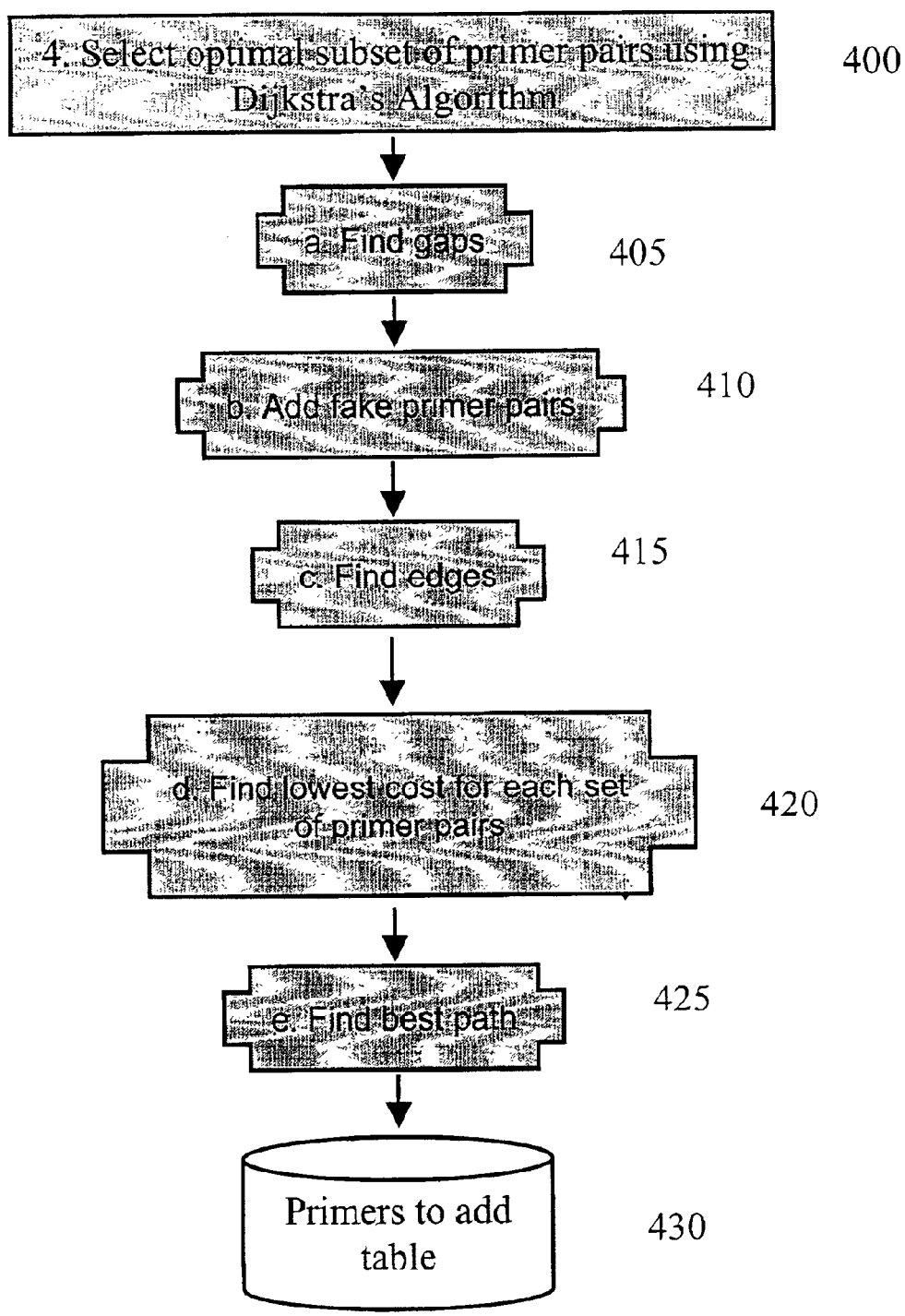
FIG. 3 shows the sub-routines utilized to select the subset of primer pairs in the fourth step of the primer pair selection process.

FIG. 3 shows greater detail of one embodiment of step 400, selecting a subset of primer pairs from the table of all primer pairs generated at step 300. Step 405 evaluates the table of all primer pairs generated at step 300, finding stretches of the target sequence where there are no primer pairs useful for amplification. Step 410 then adds fake primer pairs to cover these stretches so as to remove these gaps between primer pairs from the solution reached when applying the greedy algorithm in steps 415, 420 and 425. Step 415 determines the cost of each "edge" according to pre-selected criteria for cost, step 420 finds the lowest cost for each set of primer pairs and step 425 finds the best path for amplifying the target sequence. The subset of primers generated by steps 405, 410, 415, 420, and 425 is then stored in a file 430 on a server or similar memory device.

II. Computer System

One embodiment of the present invention provides a computer program for designing primer pairs for amplifying a target nucleic acid sequence. The computer program comprises computer code that receives input of a reference sequence; computer code that removes selected repeat regions in the reference sequence; computer code that selects primer sequences from the unremoved reference sequence; computer code that evaluates the set of primers for extent of coverage and overlap of the reference sequence; and computer code that selects a subset of primer pairs having reduced overlap from the set of primers. Preferably, the computer code that selects primer sequences from the unremoved reference sequence selects sequences according to two or more parameters including primer length and primer melting temperature to yield a set of primers.

Another embodiment of the present invention provides a system that designs primer pairs for amplifying a target nucleic acid sequence. This system comprises a processor; and a computer readable medium coupled to the processor for storing a computer program. The computer program comprises computer code that receives input of a reference sequence; computer code that removes selected repeat regions in the reference sequence; computer code that selects primer sequences from the unremoved reference sequence; computer code that evaluates the set of primers for extent of coverage and overlap of the reference sequence; and computer code that selects a subset of primer pairs having reduced overlap from the set of primers. Preferably, the computer code that selects primer sequences from the unremoved reference sequence selects sequences according to two or more parameters including primer length and primer melting temperature to yield a set of primers.

For a description of basic computer systems and computer networks, see, e.g., Introduction to Computing Systems: From Bits and Gates to C and Beyond by Yale N. Patt, Sanjay J. Patel, 1st edition (Jan. 15, 2000) McGraw Hill Text; ISBN: 0072376902; and Introduction to Client/Server Systems: A Practical Guide for Systems Professionals by Paul E. Renaud, 2nd edition (June 1996), John Wiley & Sons; ISBN: 0471133337, both are incorporated herein by reference in their entireties for all purposes.

Appendix 1 attached hereto provides an exemplary computer code in Visual Basic. This code covers taking the original sequence file (105) obtained from a public database, through adding the subset of selected primers to the primers-to-add table (step 430) (see FIGS. 1 and 2). FIG. 7 illustrates an example of a computer system that may be used to execute the software of an embodiment of the invention. FIG. 7 shows a computer system 701 that includes a display 703, screen 705, cabinet 707, keyboard 709, and mouse 711. Mouse 711 may have one or more buttons for interacting with a graphic user interface. Cabinet 707 houses a floppy drive 712, CD-ROM or DVD-ROM drive 702, system memory and a hard drive (713) which may be utilized to store and retrieve software programs incorporating computer code that implements the invention, data for use with the invention and the like. Although a CD 714 is shown as an exemplary computer readable medium, other computer readable storage media including floppy disk, tape, flash memory, system memory, and hard drive may be utilized. Additionally, a data signal embodied in a carrier wave (e.g., in a network including the Internet) may be the computer readable storage medium.

III. Amplification Reaction

In another aspect of the present invention, methods for long range nucleic acid amplification are provided, including cycling temperatures, cycling times, reagents and reagent concentrations. The methods allow for consistent long range amplification of sequences genome-wide. In some embodiments of the present invention, amplification of between about 3 kilobases and about 15 kilobases or more in length has been achieved. In some applications of the present invention, the methods result in a greater than 95% success rate for long range amplification of mammalian genomic sequences genome-wide when the reference sequence and the target sequence are from the same species. However, in addition, the methods of the present invention can be used to amplify long target sequences genome-wide in species closely-related to the species from which a reference sequence was taken. Various aspects of the present invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Figure 4:
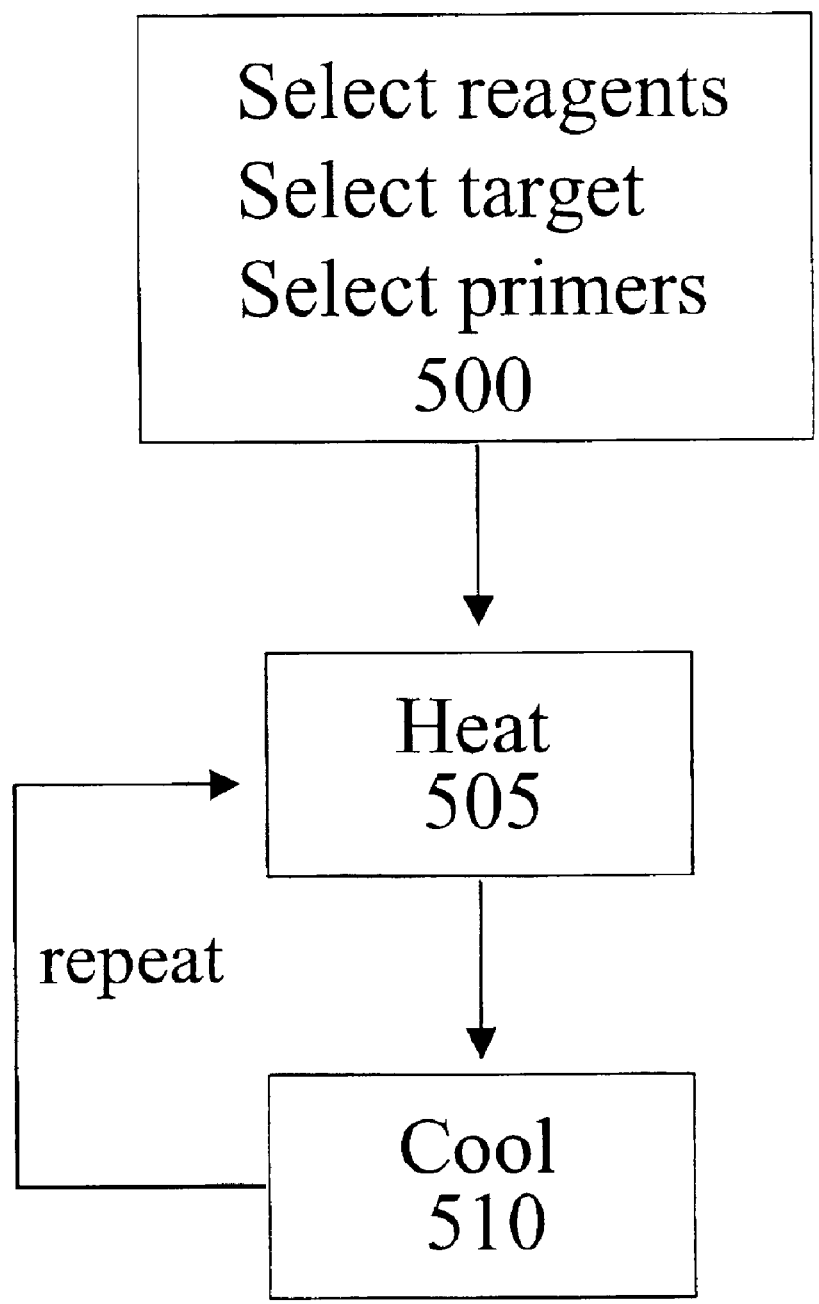
FIG. 4 shows a basic amplification process.

FIG. 4 illustrates the basic steps of an amplification reaction. In step 500 of the amplification method, reagents, target and the selected primers are combined to form a reaction mixture. The reaction mixture is then heated in step 505 to a temperature sufficient to denature the target nucleic acid, then cooled in step 510 to a temperature sufficient to allow annealing of the primers to the target and extension of the annealed primers. The heating step 505 and cooling step 510 then are repeated so as to amplify the target nucleic acid.

Also in certain embodiments of the present invention, an initial heating step may be added before the heating (505)/cooling (510) cycling where the reaction cocktail is heated at about 90° C. to about 96° C. for 1.0 to 10.0 minutes. In a preferred embodiment, this initial heating step is at about 92° C. for about 3.0 minutes. In an alternative embodiment of the present invention, the cooling time for cooling step 510 may be increased for each successive heating/cooling cycle. In one such embodiment, the cooling time is increased by about 1 to about 30 seconds in each successive cycle, and in a preferred embodiment, the cooling time is increased by about 20 seconds in each successive cycle.

In yet another embodiment of the present invention, an additional cooling step is performed after the heating (505)/cooling (510) cycle and before a final 4.0° C. cooling hold step, wherein the additional cooling step annealing/extension temperature is about 58° C. to about 65° C. and is performed for about 5 minutes to about 45 minutes. In a preferred embodiment the additional cooling step annealing/extension temperature is about 62° C. and performed for about 30 minutes.

In a specific aspect of the invention, the primers have a length of about 28 nucleotides to about 36 nucleotides and a melting temperature of about 72.0° C. to about 88.0° C. In this aspect, Tm was measured at a monovalent ion concentration of 1000 mM, a free $Mg^{++}$ concentration of 0.0 mM, a total Na$^{++}$ equivalent of 1000 mM, a nucleic acid concentration of 100 pM and where the temperature for ΔG calculations was 25° C.

In one embodiment of the present invention, the reaction cocktail resulting from step 500 comprises deoxytrinucleotide triphosphates such as dATP, dTTP, dCTP, dUTP and dGTP or mimetics thereof, target DNA, a divalent cation, DNA polymerase enzyme, a broad spectrum solvent, a zwitterionic buffer and at least one primer pair designed by the primer selection methods described above. The heating step 505 is conducted at a denaturing temperature of about 90° C. to about 96° C., preferably of about 92° C. to about 95° C., and more preferably of about 94° C. The denaturing temperature of the heating step 505 is maintained for about 1 to about 30 seconds, preferably for about 1.5 to about 5 seconds, and more preferably for about 2 seconds. The cooling step 510 is conducted at an annealing/extension temperature of about 50° C. to about 68° C., preferably of about 58° C. to about 65° C., and more preferably of about 62° C. The annealing/extension temperature is maintained for about 1 minute to about 28 minutes, and preferably for about 15 minutes. The heating and cooling steps are repeated at least about 10 times and preferably about 25 to 45 times, or more preferably about 30 to 40 times. A final cooling of the reaction cocktail to 4° C. is performed after the final cooling step 510.

In an embodiment of the present invention, the reaction cocktail comprises about 50 μM to about 400 μM of each primer in the primer pair, preferably about 100 nM to about 240 nM of each primer in the primer pair, and more preferably about 190 nM of each primer in the primer pair. In addition, the reaction cocktail comprises about 200 μM to about 500 μM each dNTP, preferably about 300 μM to about 400 μM each dNTP, and more preferably about 385 μM each DNTP. The reaction cocktail also comprises about 0.02 ng/μl to about 2.0 ng/μl template (target) DNA, preferably about 0.05 ng/μl to about 1.0 ng/μl template (target) DNA, and more preferably about 0.2 ng/μl template (target) DNA. The reaction cocktail may also comprise 0.0% to about 7.0% broad spectrum solvent, preferably 1.5% to about 4.5% broad spectrum solvent, and more preferably about 3.7% broad based solvent. In preferred embodiments, the broad based solvent is DMSO.

Further, the reaction cocktail comprises 0.0 M to about 0.75 M betaine, preferably about 0.25 M to about 0.6 M betaine, and more preferably about 0.25 M betaine, and about 7 mM to about 35 mM NH$_4$SO$_4$, preferably about 10 mM to about 20 mM NH$_4$SO$_4$, and more preferably about 13 mM NH$_4$SO$_4$. The reaction cocktail also includes about 25 mM Tris to about 125 mM Tris, preferably about 40 mM Tris to about 80 mM Tris, and more preferably about 48 mM Tris, and about 100 μM to about 500 μM MgCl$_2$, preferably about 250 μM to about 400 μM MgCl$_2$, and more preferably about 385 μM MgCl$_2$.

The reaction cocktail also comprises a polymerase. In certain embodiments, the reaction cocktail comprises about 0.01 units/μl to about 0.2 units/μl polymerase, preferably about 0.025 units/μl to about 0.07 units/μl polymerase, and more preferably about 0.05 units/μl polymerase. In addition, the reaction cocktail may comprise about 0 mM to about 50 mM zwitterionic buffer, preferably about 10 mM to about 30 mM zwitterionic buffer, and more preferably about 25 mM zwitterionic buffer. In some embodiments, the zwitterionic buffer is Tricine.

Also in some embodiments, about 0.005 μg/μl to about 0.10 μg/μl taq antibody may be added to the reaction cocktail. Preferably, about 0.01 μg/μl to about 0.05 μg/μl taq antibody is added to the reaction cocktail, and more preferably about 0.025 μg/μl taq antibody is added to the reaction cocktail.

IV. Applicability to Diverse Sequences

PCR has been applied widely in molecular biology; however, despite such wide-spread use, amplifying varying long stretches of DNA is difficult. Many protocols for long range PCR exist; however, reaction conditions are usually optimized for amplifying specific target regions of interest. Similar amplification success is not achieved when these "optimized" reaction conditions are used on different target regions. In the present invention, however, amplification of between about 3 kilobases and about 15 kilobases or more in length has been achieved on varied genomic sequences genome-wide. The methods result in excellent fidelity of amplification and product yield for mammalian target sequences in general. In some applications of the present invention, the methods result in a greater than 95% success rate for amplification of mammalian genomic sequences when the reference sequence and the target sequence are from the same species. However, in addition, the methods of the present invention can be used to amplify long target sequences genome-wide in species closely-related to the species from which a reference sequence was taken. For example, human sequence can be used to design primers that will produce long-range amplification products of non-human primates with a success rate of greater than 80%.

Figure 5:
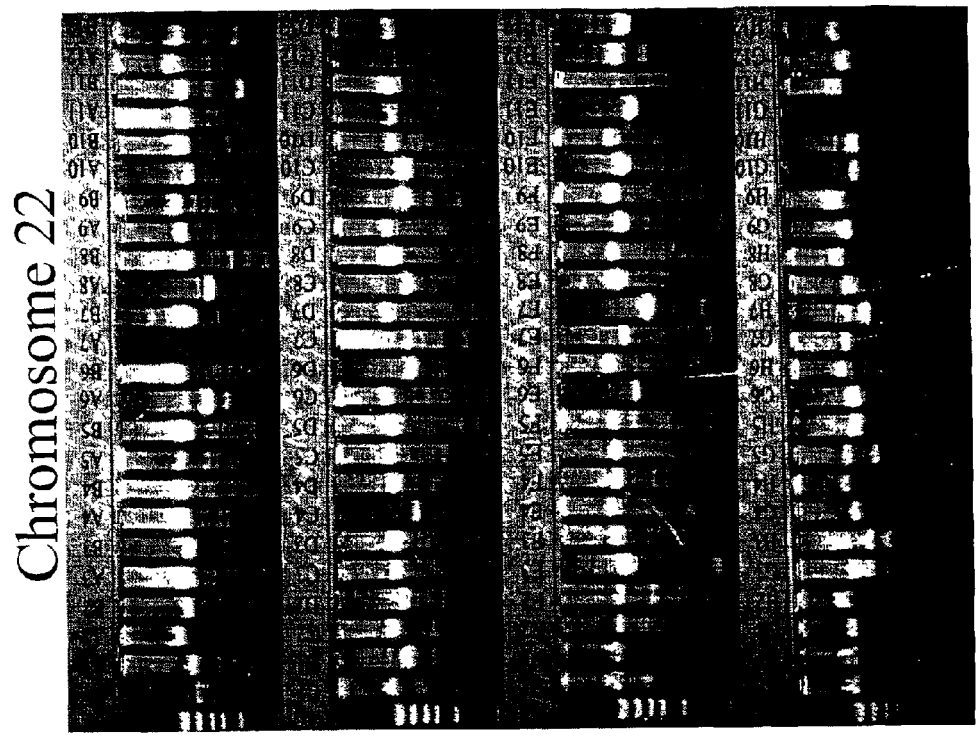
FIG. 5 shows two photographs of ethidium bromide stained agarose gels on which amplified, genomic DNAs from human chromosome 14 and chromosome 22 have been electrophoresed.
Figure 5:
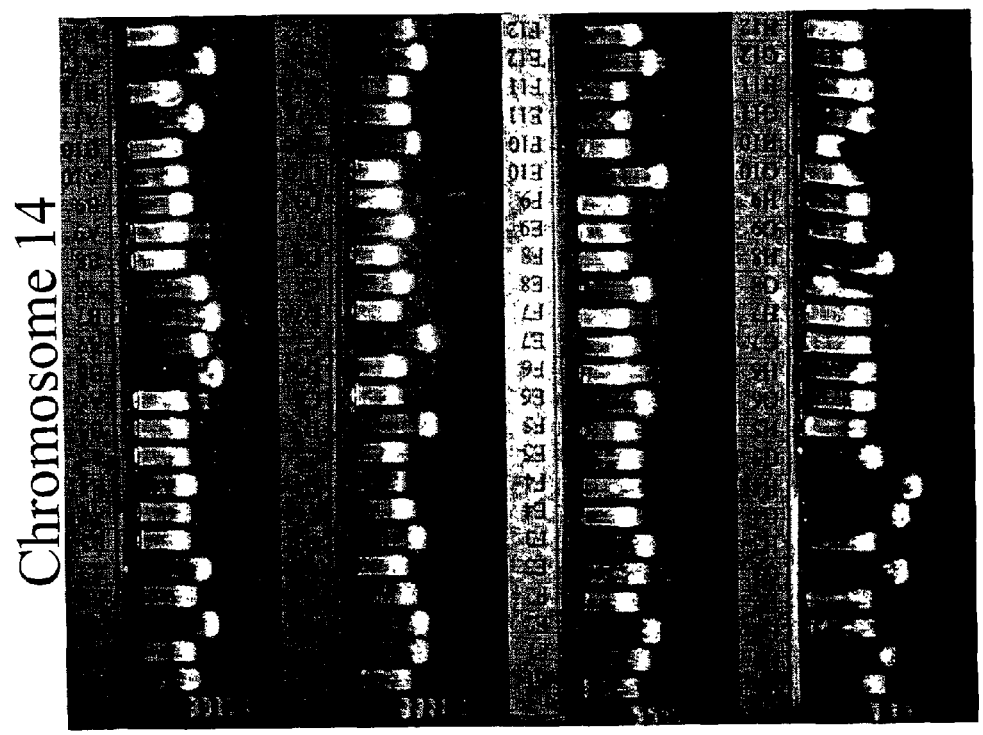
Figure 6:
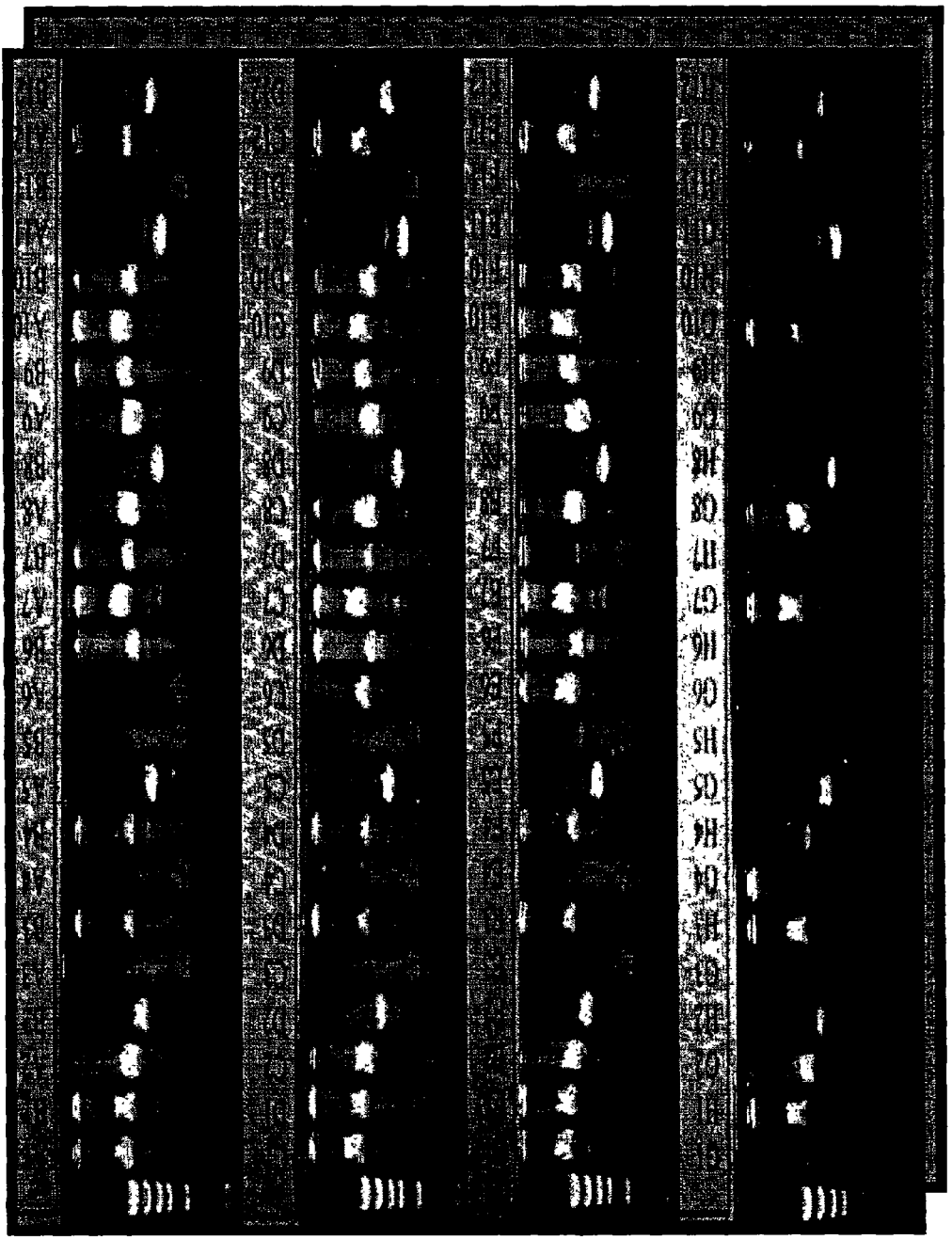
FIG. 6 shows photographs of ethidium bromide stained agarose gels on which amplified genomic DNA from human, gorilla, chimp, and macaque has been electrophoresed.

FIG. 4 shows the results obtained with the methods of the present invention for human chromosome 14 sequence used as a reference sequence for primer design and human target DNA and human chromosome 22 sequence used as a reference sequence for primer design and human target DNA. FIG. 5 shows the results obtained with the methods of the present invention with human DNA used as a reference sequence for primer design and human, gorilla, chimpanzee, and macaque genomic DNA used as target sequences.

V. Examples

The examples below illustrate specific implementations of the inventions described herein.

A. Preparation and Scoring of Somatic Cell Hybrids

Standard procedures in somatic cell genetics were used to separate human DNA strands (chromosomes) from a diploid state to a haploid state. Diploid human lymphoblast cell lines from a human diversity panel lymphoblast line (available from Coriell Cell Repositories, Camden, N.J.) were fused to a diploid hamster fibroblast cell line containing a mutation in the thymidine kinase gene. In a sub-population of the resulting fused cells, human chromosomes were introduced into the hamster calls. Selection for the human DNA-containing hamster cells (fusion cells) was achieved by utilizing HAT medium. Only hamster cells that had a stably incorporated human DNA strand grow in cell culture medium containing HAT.

Hamster cell line A23 cells were pipetted into a centrifuge tube containing 10 ml DMEM in which 10% FBCS+1X Pen/Strep+10% glutamine were added, centrifuged at 1500 rpm for 5 minutes, resuspended in 5 ml of RPMI and pipetted into a tissue culture flask containing 15 ml RPMI medium. The lymphoblast cells were grown at 37° C. to confluence. At the same time, human lymphoblast cells were pipetted into a centrifuge tube containing 10 ml RPMI in which 15% FBCS+1x Pen/Strep+10% glutamine were added, centrifuged at 1500 rpm for 5 minutes, resuspended in 5 ml of RPMI and pipetted into a tissue culture flask containing 15 ml RPMI. The lymphoblast cells were grown at 37° C. to confluence.

To prepare the A23 hamster cells, the media was aspirated and the cells were rinsed with 10 ml PBS. The cells were then trypsinized with 2 ml of trypsin and divided into 3–5 plates of fresh media (DMEM without HAT) and incubated at 37° C. The lymphoblast cells were prepared by transferring the culture into a centrifuge tube and centrifuging at 1500 rpm for 5 minutes, resuspending the cells in 5 ml RPMI and pipetting 1 to 3 ml of cells into 2 flasks containing 20 ml RPMI.

To achieve cell fusion, approximately 8–10×10$^6$ lymphoblast cells were centrifuged at 1500 rpm for 5 min. The cell pellet was then rinsed with DMEM by resuspending the cells and centrifuging them again. The lymphoblast cells were then resuspended in 5 ml DMEM. The recipient A23 hamster cells had been grown to confluence and split 3–4 days before the fusion and were, at this point, 50–80% confluent. The old media was removed and the cells were rinsed 3 times with DMEM and finally suspended in 5 ml DMEM. The lymphoblast cells were slowly pipetted over the recipient A23 cells and the combined culture was swirled slowly before incubating at 37° C. for 1 hour. After incubation, the media was gently aspirated from the A23 cells, and 2 ml room temperature PEG 1500 was added by touching the edge of the plate with a pipette and slowly adding PEG to the plate while rotating the plate with the other hand. It took approximately one minute to add all of the PEG in one full rotation of the plate. Next, 8 ml DMEM was added down the edge of the plate while rotating the plate slowly. The PEB/DMEM mixture was aspirated gently from the cells and then 8 ml DMEM was used to rinse the cells. This DMEM was removed and 10 ml fresh DMEM was added and the cells were incubated for 30 min. at 37° C. Again the DMEM was aspirated from the cells and 10 ml DMEM in which 10% FBCS and 1x Pen/Strep were added, was added to the cells, which were then allowed to incubate overnight.

After incubation, the media was aspirated and the cells were rinsed with PBS. The cells were then trypsinized and divided among 20 plates containing selection media (DMEM in which 10% FBCS+1x Pen/Strep+1x HAT were added) so that each plate received approximately 100,000 cells. The media was changed on the third day following plating. Colonies were picked and placed into 24-well plates upon becoming visible to the naked eye (day 9–14). If a picked colony was confluent within 5 days, it was deemed healthy and the cells were trypsinized and moved to a 6-well plate.

DNA and stock hybrid cell cultures were prepared from the cells from the 6-well plate cultures. The cells were trypsinized and divided between a 100 mm plate containing 10 ml selection media and an eppendorf tube. The cells in the tube were pelleted, resuspended 200 µl PBX and DNA was isolated using a Qiagen DNA mini kit at a concentration of <5 million cells per spin column. The 100 mm plate was grown to confluence, and the cells were either continued in culture or frozen.

Scoring for the presence, absence and diploid/haploid state of each hybrid was performed using the Affymetrix, Inc. HuSNP GENECHIP® (Affymetrix, Inc. of Santa Clara, Calif., GFNECHIP® HuSNP Mapping Assay, reagent kit and user manual, Affymetrix Part No. 900194), which can score 1494 markers in a single chip hybridization. As a control, the human diploid lymphoblast cell line was screened using the HuSNP chip hybridization assay, and any SNPs which were heterozygous in the parent lymphoblast diploid cell line were scored for haploidy in each fusion cell line. By comparing the markers that were present as "AB" heterozygous in the parent diploid cell line to the same markers present as "A" or "B" (hemizygous) in the hybrids, the human DNA strands which were in the haploid state in each hybrid line was determined.

B. Primer Selection

Human genomic sequence was used as a reference sequence for primer selection in this example of the present invention, and human genomic DNA derived from somatic cell hybrids was used as target DNA. In addition, in an alternative application of the present invention, human genomic sequence was used as reference sequence for primer selection and genomic DNA from gorilla and chimpanzee was used as target DNA.

FIG. 2 is a flow chart showing a detailed primer selection process according to one embodiment of the present invention. The first step 100 of primer selection required selecting a sequence of interest (target sequence or reference sequence) and creating an original sequence file (105) containing this selected sequence. Next, repeat regions in the target sequence were removed (200), and a removed file was created containing the unremoved sequence (205). In the third step, the sequences in the removed file were run through a primer pair selection program (300), and the set of all possible primers generated was stored in an oligo output file (305). The information from the oligo output file was then used to create a candidate primer pair table (315). In step four of the selection process (400), an optimal subset of primer pairs was selected from the set of all possible primer pairs in the primer pair table. The output from the selection of the optimal subset of primer pairs was stored in the primers to add table (430), which was then appended to the master database (435) and stored in an aggregate primer pair table (440).

First, human sequence to be used as the reference sequence for primer design was acquired from the Human Genome Project Working Draft team from the University of California at Santa Cruz where sequence assembly was performed using sequences obtained from the High Throughput Genomic Sequence (HTGS) database. The HTGS database is a public database with sequences contributed by, inter alia, the Human Genome Project Working Draft team. The UTSC assembly is available at the UCSC site [http://genome.cse.ucsc.edu/], and a detailed description of the data format can be found at [http://genome.cse.ucsc.edu/goldenPath/datorg.html]. Sequence was also acquired from NCBI.

In the second step, acquired reference sequence was processed by a software program called "RepeatMasker", available for licensing from the University of Washington (see:A. F. A. Smit and P. Green, [www.genome.washington.edu/uwgc/analysistools/repeatmask.htm]). RepeatMasker screens genomic sequences for repeat regions in DNA, referencing a database of known repetitive elements called RepBase. RepBase Version 5 was employed in the methods of the present invention, as were earlier versions of RepBase. The RepBase database was licensed from the Genetic Information Research Institute (see www.girinst.org). Known repetitive sequences such as Single Interspersed Nuclear Elements (SINEs, such as alu and MIR sequences), Long Interspersed Nuclear Elements (LINEs such as LINE1 and LINE2 sequences), Long Terminal Repeats (LTRs such as MaLRs, Retrov and MER4 sequences), Transposons, MER1 and MER2 sequences were "masked" or removed by the RepeatMasker program by substituting each specific nucleotide of the repeated regions (A, T, G or C) with an "N" or "X". Local nucleotide duplications were not removed. In one application of the present invention, the default settings of RepeatMasker were used, and the human.ref library (human repetitive elements) and simple.ref library were concatenated and combined to SnRNAs from the pseudo.ref library to create a "custom" library. Those skilled in the art will appreciate that any computer program, algorithm or selection process, including manual selection, which identifies and eliminates from primer selection repetitive sequences from the reference sequence may be used as an alternative to RepeatMasker.

Once the reference sequence was masked and repetitive regions removed, a third step was performed where the unremoved sequence output was then entered into the commercially-available primer design program, Oligo 6.52 using the following search parameters:
Search for: Primers and Probes
  +Strand Search
Select:
  Complex Substrate
  Compatible Pairs
  Duplex-free Oligonucleotides
  Highly Specific Oligos[3'-end stability]
  Oligonucleotide with GC Clamp
  Eliminate False Priming Oligonucleotides
  Oligonucleotides within Selected Stability Limits
  Hairpin-free Oligonucleotides
  Eliminate Homooligomers/Sequence Repeats
  Eliminate Frequent Oligos
Search Mode: Mark
PCR Product Length: 3000 to 15000
General Settings:
  High Search Stringency
  No Auto Change
  Adjust Length to Match Tm's
Parameters:
  Oligonucleotide Length: 32 nt
  Acceptable 3'-Dimer ΔG: −3.5 kcal/mol
  Maximum Length of Acceptable Dimers: 4 Base Pairs
  3'-terminal Nucleotides Checked for Dimers: 23
  3'-terminal Stability Range: −5.5 to −9.8 kcal/mol
  GC Clamp Stability: −10.0 kcal.mol
  Minimum Acceptable Loop ΔG: 0.0 kcal/mol
  Oligo Tm Range[58.1 to 108.1]:72.0 to 88.0° C.
  Max Acceptable False Priming Efficiency: 170 Points
  Min Consensus Priming Efficiency: 340 Points
  Max Acceptable Homology: 50%
  Min Consensus Homology: 95%
  Max Number of Acceptable Sequence Repeats: 3
  Max Degeneracy: 1
  Frequency Threshold: 1000
Non-Search Parameters:
  Monovalent Ion Concentration: 1000 mM
  Free $Mg^{++}$ Concentration: 0.0 mM
  Total $Na^{++}$ Equivalent: 1000 mM
  Nucleic Acid Concentration: 100 pM
  Temperature for ΔG Calculations: 25° C.
All possible primer pairs generated within the established parameters were saved to a file. Any of the generated primer pairs may be used in the amplification reactions of the present invention; however, typically primer pairs will be chosen that cover as much of the reference sequence as possible with reduced overlap.

In the present embodiment, the primer pair set output obtained from Oligo 6.52 was, in the fourth step of primer selection, subjected to Dijkstra's algorithm (again, see Introduction to Algorithms, Connen, Rivest and Leiserson (1990); ISBN 0262031418)). The goal of this step being to find a best subset of primer pairs to amplify the target sequence out of all possible sets of primer pairs generated by Oligo 6.52. Dijkstra's algorithm solves the single-source shortest path problem on a weighted, directed graph. In the embodiment of this algorithm used in applications of this invention, each primer pair was considered a "vertex" with an "edge" defined for each pair of vertices. An associated "cost" was assigned to each edge where the cost reflected the amount of 1) the overlap of vertices (cost=the length of the overlap); 2) the gap between two primer pairs (cost=10x the length of the gap); and 3) a fixed value for having to add another vertex to the set (which increased the number of primers that must be used) (cost for additional primer pair=4000). In one application of the present invention, the path with the lowest cost was selected, where total cost equals the sum of the costs of edges in the path. For example, assume three exemplary primer pairs:

|  | 5' position of the forward primer | 5' position of the reverse primer |
| --- | --- | --- |
| Primer 1: | 1000 | 2000 |
| Primer 2: | 1800 | 3000 |
| Primer 3: | 2100 | 4000 |

The "edges" are defined as being between Primer 1 and Primer 2, Primer 1 and Primer 3, and Primer 2 and Primer 3. The cost associated with the edge Primer1/Primer2 is 200+10(0)+4000=4200 (reflecting the 200 base overlap between the amplicons). The cost associated with edge Primer1/Primer3 is 0+10(100)+4000=5000 (reflecting the 100 base pair gap between Primer 1 and Primer 3). The cost associated with edge Primer2/Primer 3 would be 900+10(0)+4000=4900 (reflecting the 900 base overlap between the amplicons).

In one embodiment of the present invention, the computer code for evaluating the primer set for extent of coverage and overlap of the target sequence and selecting the subset of primer pairs was comprised of a main module, a first level subroutine, and several second level subroutines. This code is reproduced below. The main module, Main, essentially loaded the file of all possible primer pairs from the unremoved sequence from the third step, ran an error check on the sequences to assure the primers pairs were unique, ran the first level subroutine, then took the information output from the first level subroutine and appended this information to a local repository of information, which ultimately was copied to an aggregate primer pair table.

The first level subroutine, Select Optimal Primers, directed several second level subroutines, which essentially applied Dijkstra's algorithm to select a subset of primer pairs from the set of all possible primer pairs (see FIG. 3). Select Optimal Primers retrieved the information from the primer pair table (Parse Oligo Results Files), found gaps in the primer pair amplification coverage of the target reference sequence (Find Gaps 405), added fake primer pairs to cover the gaps so as not to penalize the solution for the subset selection for an unavoidable gap (Add Fake Primer Pairs for Gaps 410), determined a cost for each edge (Find Edges 415), computed the lowest cost for every possible set of primer pairs (Compute Minimum Costs 420), found the best subset of primer pairs (Find Best Path 425), and added this subset of primer pairs to a local repository (430) that was then added to the final aggregate repository of primer pairs (440).

C. Amplification Reaction

The amplification reaction involves both an amplification reaction mix or cocktail and thermocycling parameters. In one application of the present invention, the reaction mix was prepared by making two master reaction mixes, then adding an aliquot of each mix to the primer pairs in the following manner:

PCR Set Up:
13 µL total volume reactions

| Reagents: | Amount per reaction | Final Concentration per reaction |
|---|---|---|
| Master Mix 1: | | |
| Water | 4.775 µL | |
| dNTPs, 10 mM each | 0.5 µL | 385 µM |
| template DNA (20 ng/µL) | 0.1 µL | 2 ng |
| 10% DMSO/5 M betaine | .625 µL | 0.48x |
| Total Volume: | 6 µL | |
| Master Mix 2: | | |
| Water | 3.5625 µL | |
| 140 mM NH$_4$SO$_4$/500 mM Tris | 1.25 µL | 13 mM/48 mM |
| 25 mM MgCl$_2$ | 2.7 µL | 385 µM |
| Taq Polymerase (2.5 U/µL) | 0.2625 µL | 0.66 units |
| DMSO | 0.4 µL | 3.1% |
| Tricine (1 M) | 0.325 µL | 25 mM |
| Total Volume: | 6.0 µL | |

The Master Mixes were prepared and kept on ice. 6.0 µL of each Master Mix was added to tubes containing 1 µL of the primers where the primers contained 2.5 µM of each of the forward and reverse primers for a final concentration of 192 nM each primer in the final 13 µL reaction volume.

In an alternative embodiment of the present invention, the taq polymerase can be eliminated from Master Mix 2, and instead combined with 0.015 µg/µL TaqStart antibody and buffer to form an antibody-bound taq complex which is then added to the reaction cocktail after the Master Mix 1 and 2 have been combined.

Reagents for the reaction cocktails can be obtained from the following sources: dNTP's (Life Technologies), Taq polymerase (Roche Molecular Biosciences, Epicentre Tecnlogies, Biorad Laboratories or Applied Biosystems), tricine, tris, NH$_4$SO$_4$, MgCl$_2$, betaine, and DMSO (Sigma Aldrich), Taqstart antibody (Clontech).

In one example, the cycling conditions were as follows:
Initial heating step: 94° C. for 3 minutes
10 cycles of: heating step: 94° C. for 2 seconds
  cooling step: 62° C. for 15 minutes
28 cycles of: heating step: 94° C. for 2 seconds
  cooling step: 62° C. for 15 minutes for the first cycle, with an increase in time of 20 seconds in each subsequent cycle
Final cooling step: 62° C. for 25 minutes 4° C. hold
Also, in an alternative example of the present invention, the cycling conditions were as follows:
Initial heating step: 94° C. 3 minutes
35 cycles of: heating step: 94° C. for 2 seconds
  cooling step: 62° C. for 12 minutes
Final cooling step: 62° C. for 25 minutes 4° C. hold
Aliquots of each completed amplification reaction were run on a 0.8% agarose gel and visualized with ethidium bromide.

The above description is illustrative and not restrictive. Many variations of the invention will become apparent to those of skill in the art upon review of this disclosure. The scope of the invention should, therefore, be determined with reference to the appended claims along with their full scope of equivalents.

APPENDIX 1

```
°Copyright, Perlegen Sciences, Inc., All Rights Reserved
MAIN MODULE:
MAIN - Parse And Select Primers - this routine drives everything
' ====    =========================
"  Upon start-up, run this routine. Check the table "PPC" to find out whether
'  to start a contig. (Populated "PPC" <= => don't start). If "PPC" is empty,
'  this process will attempt to process a batch of primer pairs (for a contig).
'  It will do these steps:
'
'  (A) Parse the OLIGO files for this contig -> table "PPC" (see below)
'  (B) Select unique primer pairs from "PPC" -> table "PrimerPair"
'  (C) Run "SelectOptimalPrimerPairs": PP's -> table "PrimersToAdd"
'  (D) Append primer pairs from PrimersToAdd -> table "Primers"
'  (below)
'
'  This database is assumed to have a contig for its name. That's how it knows
'  which contig to do. Also, it needs to have the following linked tables:
'
'  (1) ChrInfo:   Information specific to this chromosome
'  (2) CtgInfo:   Lengths of all contigs for this chromosome
'  (3) Primers:   Where to append the selected primer pairs
''''''''''''''''''''''''''''''''''''''''''''''''''
Option Compare Database
Option Explicit
'  Only Functions can be called in AutoExec Macro!
Public Function ParseAndSelectPrimers( ) As Boolean
        Dim rst As Recordset
        Dim strPath As String
        Dim strContig As String
        Dim strPrefix As String
        Dim lngContigLen As Long
        Dim lngSegmentLen As Long
        Dim lngOverlap As Long
        Dim lngSeqID As Long
        Dim NumPPs As Long
        '  Find out whether to do anything:
        Set rst = CurrentDb.OpenRecordset("PPC")
        If rst.RecordCount < > 0 Then
                DoCmd.OpenForm "frmNotes"
                Exit Function
        End If
        Set rst = Nothing
        '  Initialize:
        strPath = GetItemValue ("OligoResultsPath")
        strContig = GetContig
        strPrefix = GetItemValue("FileNamePrefix")
        lngContigLen = GetContigLen (strContig)
        lngSegmentLen = GetItemValue ("SegmentLength")
        lngOverlap = GetItemValue ("Overlap")
        lngSeqID = GetItemValue ("SeqID")
        '  (A)
        WriteLog "STARTING . . ."
        WriteLog "ParseOligoFileSet" & strPath & strContig & " - Length: " & lngContigLen
        NumPPs = ParseOligoFileSet (strPath, strContig, strPrefix, lngContigLen, lngSegmentLen, lngOverlap, lngSeqID)
        '  (B)
        WriteLog NumPPs & " primer pairs found. Append unique ones to PrimerPair . . ."
        CurrentDb.Execute "Append PPC -> PrimerPair"
        '  (C)
        WriteLog "SelectOptimalPrimerPairs"
        SelectOptimalPrimerPairs
        '  (D)
        WriteLog "Append PTA -> Primers"
        CurrentDb.Execute "Append PTA -> Primers"
        '  That's it:
        WriteLog "Application Quit - " & strContig
        Application.Quit
End Function
```

APPENDIX 1-continued

FIRST LEVEL SUBROUTINE: SELECT OPTIMAL PRIMER PAIRS

```
Option Compare Database
Option Explicit
' Find optimal bunch of primer pairs:
' Assume PrimerPair is ready (local) and Edge is not indexed and Gap exists
Public Sub SelectOptimalPrimerPairs ( )
        WriteLog "FindGaps"
        FindGaps
        WriteLog "AddFakePrimerPairsToCoverTheGaps"
        AddFakePrimerPairsToCoverTheGaps
        WriteLog "FindEdges"
        FindEdges
        WriteLog "CreateIndexes"
        IndexFieldInTable "Src", "Edge"
        IndexFieldInTable "Dst", "Edge"
        IndexFieldInTable "Cost", "Edge"
        WriteLog "Executing queries - ZeroOut COST, etc."
        CurrentDb.Execute "ZeroOut COST, PRED, DONE"
        CurrentDb.Execute "ZeroOut COST of PP0"
        WriteLog "ComputeMinCosts"
        ComputeMinCosts
        WriteLog "Initialize field 'SELECTED'"
        RenameFieldInTable "DONE", "SELECTED", "PrimerPair"
        CurrentDb.Execute "UPDATE PrimerPair SET SELECTED = No"
        WriteLog "FindBestPath"
        FindBestPath
        WriteLog "Queries - Make Selected, PrimersToAdd"
        CurrentDb Execute "Make Selected"
        CurrentDb Execute "Make PrimersToAdd"
        WriteLog "Skipping ~ FindActualGaps - can run on main machine!"
        ' Skip - FindActualGaps
        ' 'WriteLog "FINISHED.' "
        ' 'MsgBox "Primer Pair Optimizer finished!", vbInformation, Now
End Sub
SECOND LEVEL SUBROUTINES:
1. PARSE OLIGO RESULTS
Parse Oligo Results File(s):
'
' ==========================
' Get primer pairs from Oligo results files. Store them locally (table "PPC").
' Specifically, get ALL the primer pairs for a chromosome (many contigs).
'
' Assumptions: (1) OLIGO results filenames are like [Startbase].txt
'
'''''''''''''''''''''''''''''''''''''''''
Option Compare Database
Option Explicit
' Parse an OLIGO results file SET (all for one contig):
Public Function ParseOligoFileSet(ByVal strOligoParentPath As String,
ByVal strContig As String, _ByVal strFileNamePrefix As String, ByVal
lngContigLen As Long, _ByVal lngSegmentLen
As Long, ByVal lngOverlap As Long,
_ByVal lngSeqID As Long) As Long
        Dim I As Long
        Dim strFileName As String
        ' Initialize:
        ParseOligoFileSet = 0
        ' Parse the primer pairs:
        For I = 1 To lngContigLen - lngOverlap Step lngSegmentLen - lngOverlap
                strFileName = strOligoParentPath & strContig & "\" & CStr(I) & ".txt"
                Say "Primer pairs found: " & ParseOligoFileSet & ": Parsing" & strFileName
                ParseOligoFileSet = ParseOligoFileSet + ParseOligoFile (strFileName, strContig, I, strFileNamePrefix, lngSeqID)
        Next I
        ' Done:
        Say "Ready"
End Function
' Write primer pairs to table "PPC":
Private Function ParseOligoFile(ByVal strFileName As String,
ByVal strContig As String, ByVal lngStartBase As Long, _ByVal
strFileNamePrefix As String, ByVal lngSeqID As Long) As Long
        Dim rst As Recordset
        Dim iFileNum As Integer
        Dim strLine As String
        Dim lngPairNum As Long
        Dim lngPrimerLen As Long
        Dim nColonPosn As Long
        Dim nLetterPosn As Long
        Dim nThreePosn As Long
        ' Open the table:
        Set rst = CurrentDb.OpenRecordset ("PPC")
        With rst
                ' Open the file:
                iFileNum = FreeFile
                Open strFileName For Input As #iFileNum
                ' Verify that the file ID matches the file name in line 2 of the Oligo file:
                Line Input #iFileNum, strLine
                Line Input #iFileNum, strLine
                If lngStartBase < > CLng(Getsubstring(1, strLine, strFileNamePrefix, "_")) Then
                        MsgBox lngStartBase & "not found in" & strLine, vbCritical, "Possible Parsing Problem"
                        Stop
                End If
                ' Get all the primer pairs:
                Do Until EOF(iFileNum)
                        ' Input & line from the file:
                        Line Input #iFileNum, strLine
                        ' Check for new primer pair:
                        If Left$(strLine, 6) = "Pair #" Then
                                ' Add the new pair:
                                .AddNew
                                !SequenceID = lngSeqID
                                !Contig = strContig
                                !FileID = lngStartBase
                                lngPairNum = CLng(Mid$(strLine, 7))
                                !PairNum = lngPairNum
                                ' Product Length:
                                Line Input #iFileNum, strLine
                                !AmpliconLen = Val(Mid$(strLine, 16))
                                ' Forward Coordinates:
                                SkipLines 3, iFileNum
                                Line Input #iFileNum, strLine
                                nColonPosn = InStr(strLine, ":")
                                nLetterPosn = InStr(strLine, "U")
                                !FPOS = lngStartBase + CLng (Mid$(strLine, nColonPosn + 1, nLetterPosn - (nColonPosn + 1))) -1
                                !ForwardLen = Val(Mid$(strLine, nLetterPosn + 1))
                                "Forward Sequence:
                                Line Input #iFileNum, strLine
                                nThreePosn = InStr(strLine, "3")
                                !ForwardSeq = RemoveWhiteSpace (Snip(strLine, 4, nThreePosn))
                                ' Forward Tm:
                                Line Input #iFileNum, strLine
                                !ForwardTm = Val(Mid$(strLine, 4))
                                ' Reverse Coordinates:
                                SkipLines 4, iFileNum
                                Line Input #iFileNum, strLine
                                nColonPosn = InStr(strLine, ":")
                                nLetterPosn = Instr(strLine, "L")
                                lngPrimerLen = Val(Mid$(strLine, nLetterPosn + 1))
                                !REND = lngStartBase + CLng (Snip(strLine, nColonPosn + 1, nLetterPosn)) + lngPrimerLen - 2
                                !ReverseLen = lngPrimerLen
                                ' Reverse Sequence:
                                Line Input #iFileNum, strLine
                                nThreePosn = InStr(strLine, "3")
                                !ReverseSeq = RemoveWhiteSpace (Snip(strLine, 4, nThreePosn))
                                ' Reverse Tm:
                                Line Input #iFileNum, strLine
                                !ReverseTm = Val(Mid$(strLine, 4))
                                ' Update:
                                .Update
                        End If
                Loop
```

APPENDIX 1-continued

```
                End With
                Set rst = Nothing
                Close #iFileNum
                '  Return the number of pairs parsed (i.e., the most recent
pair):
                ParseOligoFile = lngPairNum
End Function
2. FIND GAPS
Option Compare Database
Option Explicit
Public Sub FindGaps( )
            Dim lngMaxREND As Long
            Dim lngREND As Long
            Dim lngFPOS As Long
            Dim sSQL As String
            Dim rstMain As Recordset
            Dim rstGap As Recordset
            Say "Finding the gaps . . ."
            sSQL = "SELECT * FROM PrimerPair order by FPOS,
PPCID"
            Set rstMain = CurrentDb.OpenRecordset(sSQL)
            Set rstGap = CurrentDb.OpenRecordset("Gap")
            With rstMain
                lngMaxREND = 0
                Do Until .EOF
                    lngREND = !REND
                    lngFPOS = !FPOS
                    '  Check for gap:
                    If lngMaxREND + 1 < lngFPOS Then
                        With rstGap
                            .AddNew
                            !LastREND = lngMaxREND
                            !NextFPOS = lngFPOS
                            !NextPPCID = rstMain!PPCID
                            .Update
                        End With
                    End If
                    '  Update Max REND:
                    If lngMaxREND < lngREND Then
                        lngMaxREND = lngREND
                    End If
                    '  Status:
                    If .AbsolutePosition Mod 1000 = 0 Then
                        Say "Finding Gaps: " &
.AbsolutePosition
                    End If
                    .MoveNext
                Loop
                '  Fake a gap from Max REND to ONE BILLION:
                With rstGap
                    .AddNew
                    !LastREND = lngMaxREND
                    !NextFPOS = 1000000000
                    .Update
                End With
            End With
            Set rstMain = Nothing
            Set rstGap = Nothing
            Say "Ready"
End Sub
3. ADD FAKE PRIMER PAIRS FOR GAPS
Option Compare Database
Option Explicit
Public Sub AddFakePrimerPairsToCoverTheGaps( )
            Dim lngPPCID As Long
            Dim rstGap As Recordset
            Dim rstPP As Recordset
            Set rstGap = CurrentDb.OpenRecordset("SELECT *
FROM Gap ORDER BY LastREND")
            Set rstPP = CurrentDb.OpenRecordset ("PrimerPair")
            Say "Adding fake PP's to cover the gaps . . ."
            lngPPCID = 0   '  Woe to you who changes this line
            Do Until rstGap.EOF
                With rstPP
                    .AddNew
                    !PPCID = lngPPCID
                    !FPOS = rstGap!LastREND
                    !REND = rstGap!NextFPOS
                    .Update
```

APPENDIX 1-continued

```
                End With
                lngPPCID = lngPPCID = 1  '  Avoid positive ID's
(used already)
                rstGap.MoveNext
            Loop
            Set rstGap = Nothing
            Set rstPP = Nothing
            Say "Ready"
End Sub
4. FIND EDGES
Option Compare Database
Option Explicit
'  How much worse is a skipped base than an overlapping base:
Private Const mcnGapPenaltyPerBase As Long = 10
'  How much worse is an additional amplicon than an overlapping base:
Private Const mcnPenaltyPerAmplicon As Long = 4000
'  Populate the Edge table with costs of amplicon pairing:
Public Sub FindEdges( )
            Dim rstSrc As Recordset
            Dim rstDst As Recordset
            Dim rstEdge As Recordset
            Dim sSQL As String
            Dim lngSrcID As Long
            Dim lngSrcFPoS As Long
            Dim lngSrcREND As Long
            Say "Finding Edges - Initializing Recordset . . ."
            sSQL = "SELECT * FROM PrimerPair ORDER BY FPOS,
REND"
            Set rstSrc = CurrentDb.OpenRecordset(sSQL)
            Set rstEdge = CurrentDb.OpenRecordset("Edge")
            Do Until rstSrc.EOF
                lngSrcFPOS = rstSrc!FPOS
                lngSrcREND = rstSrc!REND
                lngSrcID = rstSrc!PPCID
                If lngSrcID Mod 11 = 0 Then
                    Say "Finding Edges for " & lngSrcID
                End If
                sSQL = "SELECT * FROM PrimerPair WHERE" & _
                    " FPOS > " & lngSrcFPOS & "AND" & _
                    " REND > " & lngSrcREND & "AND" & _
                    " FPOS < " & lngSrcREND + 1000 & _
                    " ORDER BY FPOS, REND "
                Set rstDst = CurrentDb.OpenRecordset(sSQL)
                Do Until rstDst.EOF
                    With rstEdge
                        .AddNew
                        !Src = lngSrcID
                        !Dst = rstDst!PPCID
                        !COST = GetCost(lngSrcREND,
rstDst!FPOS)
                        .Update
                    End With
                    rstDst.MoveNext
                Loop
                rstSrc.MoveNext
            Loop
            Set rstSrc = Nothing
            Set rstDst = Nothing
            Set rstEdge = Nothing
            Say "Ready"
End Sub
5. COMPUTE MINIMUM COSTS
Option Compare Database
Option Explicit
Public Sub ComputeMinCosts( )
            Dim lngMinSrcCost As Long
            Dim lngSrcID As Long
            Dim lngEdgeCost As Long
            Dim sSQL As String
            Dim rstMin As Recordset
            Dim rstSrc As Recordset
            Dim rstEdge As Recordset
            Dim rstDst As Recordset
            Say "Starting Computation of Min Costs . . ."
            Do
                '  Find the next lowest cost vertex:
                sSQL = "SELECT Min(COST) FROM PrimerPair
WHERE DONE = No"
                Set rstMin = CurrentDb.OpenRecordset(sSQL)
```

APPENDIX 1-continued

```
        If IsNull(rstMin.Fields(0)) Then Exit Do ' Exit here!
        lngMinSrcCost = rstMin.Fields(0)
        sSQL = "SELECT TOP 1 PPCID, DONE FROM
PrimerPair WHERE DONE = No AND COST = " & lngMinSrcCost
        Set rstSrc = CurrentDb.OpenRecordset(sSQL)
        lngSrcID = rstSrc.Fields(0)
        ' Traverse all edges from that vertex:
        If lngSrcID Mod 20 = 0 Then
            Say "Traversing all edges from " & lngSrcID
        End If
        sSQL = "SELECT * FROM Edge WHERE
Src =" & lngSrcID
        Set rstEdge = CurrentDb.OpenRecordset(sSQL)
        Do Until rstEdge.EOF
            ' Edge cost:
            lngEdgeCost = rstEdge!COST
            ' Destination:
            sSQL = "SELECT * FROM PrimerPair
WHERE PPCID = " & rstEdge!Dst
            Set rstDst = CurrentDb.OpenRecordset(sSQL)
            ' See if the destination has a better path to it:
            If lngMinSrcCost + lngEdgeCost <
rstDst!COST Then
                With rstDst
                    .Edit
                    !COST = lngMinSrcCost +
lngEdgeCost
                    !PRED = lngSrcID
                    .Update
                End With
            End If
            rstEdge.MoveNext
        Loop
        ' Now that vertex is DONE:
        rstSrc.Edit
        rstSrc!DONE = True
        rstSrc.Update
    Loop
    Set rstMin = Nothing
    Set rstSrc = Nothing
    Set rstEdge = Nothing
    Set rstDst = Nothing
    Say "Ready"
End Sub
6. FIND BEST PATH
Option Compare Database
Option Explicit
' Flag PrimerPairs as SELECTED, starting at the END and working
backwards, until there is no Predecessor:
    ' Assume there is a record with REND = 1000000000
    Public Sub FindBestPath( )
        Dim sSQL As String
        Dim rstPP As Recordset
        Dim vntPredID As Variant
        Say "Selecting Optimal Primer Pairs . . ."
        sSQL = "SELECT * FROM PrimerPair WHERE REND =
1000000000"
        Do
            Set rstPP = CurrentDb.OpenRecordset(sSQL)
            With rstPP
                .Edit
                !SELECTED = True
                .Update
            End With
            vntPredID = rstPP!PRED
            sSQL = "SELECT * FROM PrimerPair WHERE
PPCID = " & vntPredID
        Loop Until IsNull(vntPredID)
        Set rstPP = Nothing
        Say "Ready"
    End_Sub
    ' New Get Cost function (starting with chr 20):
    Private Function GetCost(ByVal lngSrcREND As Long, ByVal
lngDstFPOS As Long) As Long
        If lngSrcREND < lngDstFPOS Then
            GetCost = (lngDstFPOS − lngSrcREND) *
mcnGapPenaltyPerBase
        ' Gap cost
        Else
            GetCost = lngSrcREND − lngDstFPOS
        ' Overlap cost
        End if
        GetCost = GetCost + mcnPenaltyPerAmplicon
    ' Amplicon cost
End Function
```

What is claimed is:

1. A method for designing primer pairs for amplifying a target nucleic acid sequence using a reference sequence, comprising the steps of:
choosing said reference sequence;
removing at least selected repeal regions in said reference sequence thereby yielding removed and unremoved regions of said reference sequence;
selecting primer sequences from said unremoved regions of said reference sequence according to two or more parameters including primer length and primer meeting temperature to yield a set of primers;
evaluating said set of primers for extent of coverage and overlap of said reference sequence; and
selecting a subset of primer pairs having reduced overlap from said set of primers, such that amplicons corresponding to said subset of primer pairs overlap by less than about 5%, and wherein said primer pairs in said subset have been thereby designed for amplifying said target nucleic acid sequence.

2. The method of claim 1, wherein said primer length is selected to be between about 28 nucleotides and about 36 nucleotides.

3. The method of claim 1, wherein said primer melting temperature is between about 72° C. and about 88° C.

4. The method of claim 1, wherein said two or more parameters from said first selecting step is selected from the group of stringency, duplex existence, specificity, GC clamp, hairpin existence, sequence repeal existence, dissociation minimum for 3' dimer, dissociation minimum 3' terminal stability range, dissociation minimum for minimum acceptable loop, percent maximum homology, percent consensus homology, maximum number of acceptable sequence repeals, frequency threshold, and maximum length of acceptable dimers.

5. The method of claim 1, wherein said extent of coverage is above about 90% of said reference sequence.

6. The method of claim 1, wherein said removing step is performed by a computer program.

7. The method of claim 1, wherein said first selecting step is performed by a computer system.

8. The method of claim 1, wherein said second selecting step selects a subset of primer pairs with a least number of primer pairs required to amplify said target sequence.

9. The method of claim 1, wherein said second selecting step selects said subset of primer pairs according to at least one parameter selected from the group of overlap length, gaps between pairs of primer pairs, and necessity of adding another primer pair to the subset.

10. The method of claim 8 or 9, wherein said second step is performed by a computer system.

11. The method of claim 1, wherein a computer program executes a single-source shortest-path algorithm to select said subset of primer pairs.

12. The method of claim 11, wherein said computer program executes an algorithm solving a single-source shortest path problem on a weighted, directed graph $G=(V, E)$ for the case in which all edge weights are nonnegative, and $w(u,w)>0$ for each edge $(u,v) \in E$.

13. The method of claims 1, wherein a computer program executes a greedy algorithm to select said subset of primer pairs.

14. The method of claim 1, wherein said target sequence is genomic DNA from a human species.

15. The method of claim 1, wherein said target sequence is genomic DNA from a non-human primate species.

16. The method of claim 1, wherein said reference sequence is genomic DNA from a human species.

17. The method of claim 1, wherein said primer length is about 28 nucleotides to about 36 nucleotides and said melting temperature is about 72° C. to about 88° C.

18. A computer-implemented method for designing primer pairs for amplifying a target nucleic acid sequence comprising:

inputting a reference sequence into a computer program, wherein said computer program is designed to recognize regions that are repeated in said reference sequence, removing selected repeat regions in said reference sequence to yield removed and unremoved reference sequence;

selecting primer sequences from said unremoved reference sequence according to two or more parameters including primer length and primer melting temperature to yield a set of primers;

evaluating said set of primers for extent of coverage and overlap of said reference sequence; and selecting a subset of primer pairs having reduced overlap from said set of primers such that amplicons corresponding to said subset of primer pairs overlap by less than about 5%, and wherein said primer pairs in said subset have been thereby designed for amplifying said target nucleic acid sequence.

19. The method of claim 18, wherein said removing step is performed by said computer program, and wherein said computer program further references a database.

20. The method of claim 18, wherein said selecting primer sequences in said first selecting step uses additional parameters selected from the group of stringency, duplex existence, specificity, GC clamp, hairpin existence, sequence repeat existence, dissociation minimum for 3' dimer, dissociation minimum 3' terminal stability range, dissociation minimum for minimum acceptable loop, percent maximum homology, percent consensus homology, maximum number of acceptable sequence repeats, frequency threshold, and maximum length of acceptable dimers.

21. The method of claim 18, wherein a second computer program executes an algorithm that in said second selecting step selects a subset of primer pairs according to at least one parameter selected from the group of overlap length, gaps between pairs of primer pairs, and necessity of adding another primer pair to the subset.

22. The method of claim 18, wherein in said second selecting step a second computer program executes an algorithm that selects said subset of primer pairs according to at least one parameter selected from the group of overlap length, gaps between pairs of primer pairs, and necessity of adding another primer pair to the subset.

23. The method of claim 18, wherein in said second selecting step a second computer program executes a single-source shortest-path algorithm.

24. The method of claim 18, wherein in said second selecting step a second computer program executes Dijkstra's algorithm.

25. A system that designs primer pairs for amplifying a target nucleic acid sequence comprising:

a processor; and a computer readable medium coupled to said processor for storing a computer program comprising: computer code that receives input of a reference sequence; computer code that removes at least selected repeat regions in said reference sequence to yield removed and unremoved reference sequence; computer code that selects primer sequences from said unremoved reference sequence according to two or more parameters including primer length and primer melting temperature to yield a set of primers; computer code that evaluates said set of primers for extent of coverage and overlap of said reference sequence; and computer code that selects a subset of primer pairs having reduced overlap from said set of primers such that amplicons corresponding to said subset of primer pairs overlap by less than about 5%, and wherein said primer pairs in said subset have been thereby designed for amplifying said target nucleic acid sequence.

* * * * *

SEQUENCE LISTING

<160> NUMBER OF SEQ ID NOS: 2

<210> SEQ ID NO 1
<211> LENGTH: 855
<212> TYPE: DNA
<213> ORGANISM: Human

<400> SEQUENCE: 1

```
caactaaaag tcacaaaagc catggaaaat agtctcaggg atacacatct gctcttcaga      60
ttctgaattc tggtcttgca tgatttcttt caccaggagc cagcagagct gtgcttcctc     120
ggactaacaa cttgcccctc actccctacc ctccgggcac cgtctcctct ataaagtcac     180
cctctcagct tttctttatc cccagagatg acacaaatac agagaactgt ggcatttta      240 tagcatttag gtgaaagatg ttataaatta tacagttcac ctgagagaaa aaatacatgc     300
taaaccaggc agtgcctcac acctgtaatc ccagcatttg gggaggccaa agcgggagga     360
ttgcttcagc ccagagttca agatcagact gggcaacaca gtgagacctc ttctctacaa     420
aaaaaaaaaa aatcaaaaaa tgaaggagga tcacttgagc tctggaggtt gaggctgcaa     480
```

-continued

```
tgagccatga ttgcaccatt gcactcttgc ctgggtgaca gagtgagacc ctgcctcaaa      540
aaaaaaataa ataaataaat agaaagaaag aaagaaaatg aaagaagaaa atccatgtga      600
ataatcttat tctagcaaat aaggatgtta gaatgcagca tattaaaata ttacaaaagt      660
acaatactat gaaaaaatat ggcactcaac acagagcaga atggaaacta gaattgaaca      720
gaggaaagta ttttgaactc ctgagtgcag gataggtttt tttcaataga tggtattggg      780
acaactattt gaaacaaaaa agaaatgtag atccactaaa tgaattgttc ctggaataca      840
gacttaaata gataa                                                       855

<210> SEQ ID NO 2
<211> LENGTH: 855
<212> TYPE: DNA
<213> ORGANISM: Human
<220> FEATURE:
<221> NAME/KEY: misc_feature
<222> LOCATION: (306)...(433)
<223> OTHER INFORMATION: n = A,T,C or G
<220> FEATURE:
<221> NAME/KEY: misc_feature
<222> LOCATION: (444)...(607)
<223> OTHER INFORMATION: n = A,T,C or G

<400> SEQUENCE: 2
caactaaaag tcacaaaagc catggaaaat agtctcaggg atacacatct gctcttcaga       60
ttctgaattc tggtcttgca tgatttcttt caccaggagc cagcagagct gtgcttcctc      120
ggactaacaa cttgcccctc actccctacc ctccgggcac cgtctcctct ataaagtcac      180
cctctcagct tttctttatc cccagagatg acacaaatac agagaactgt ggcattttta      240
tagcatttag gtgaaagatg ttataaatta tacagttcac ctgagagaaa aaatacatgc      300
taaacnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnncaaaaaa tgannnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnntat tctagcaaat aaggatgtta gaatgcagca tattaaaata ttacaaaagt      660
acaatactat gaaaaaatat ggcactcaac acagagcaga atggaaacta gaattgaaca      720
gaggaaagta ttttgaactc ctgagtgcag gataggtttt tttcaataga tggtattggg      780
acaactattt gaaacaaaaa agaaatgtag atccactaaa tgaattgttc ctggaataca      840
gacttaaata gataa                                                       855
```